US010071098B2

(12) United States Patent
Clifford et al.

(10) Patent No.: US 10,071,098 B2
(45) Date of Patent: *Sep. 11, 2018

(54) COMPOSITIONS USEFUL FOR TREATING HERPES SIMPLEX LABIALIS AND/OR HERPES ESOPHAGITIS, AND METHODS USING SAME

(71) Applicant: DREXEL UNIVERSITY, Philadelphia, PA (US)

(72) Inventors: Jane E. Clifford, Newtown, PA (US); William E. Donegan, Philadelphia, PA (US); Oleg Alekseev, Philadelphia, PA (US)

(73) Assignee: Drexel University, Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/864,434

(22) Filed: Sep. 24, 2015

(65) Prior Publication Data
US 2016/0089372 A1    Mar. 31, 2016

Related U.S. Application Data

(60) Provisional application No. 62/055,994, filed on Sep. 26, 2014.

(51) Int. Cl.
*A61K 31/522* (2006.01)
*A61K 31/535* (2006.01)
(Continued)

(52) U.S. Cl.
CPC ............ *A61K 31/522* (2013.01); *A61K 31/00* (2013.01); *A61K 31/4184* (2013.01); *A61K 31/5377* (2013.01)

(58) Field of Classification Search
CPC .................... A61K 31/5377; A61K 31/522
(Continued)

(56) References Cited

U.S. PATENT DOCUMENTS

| 2009/0124639 | A1  | 5/2009 | Oyewumi et al. |
|---|---|---|---|
| 2010/0035811 | A1* | 2/2010 | Kim ................ A61K 31/663 514/6.9 |
| 2010/0143440 | A1  | 6/2010 | Prichard et al. |

FOREIGN PATENT DOCUMENTS

| DE | 19832519 A1 * | 1/2000 |
|---|---|---|
| GB | 2310139 A | 8/1997 |

OTHER PUBLICATIONS

Yamamoto et al. "ATM activation is indispensible in HSV, but ATM/ATR activation is not necessary in VZV for efficient replication," Journal of Dermatological Science, 2010, vol. 60, No. 3, pp. e40, Abstract No. p. 12-04, Meeting info: 35th Annual Meeting of Japanese Society of Investigative Dermatlogy, JSID 2010. Wakayama, Japen. Dec. 3, 2010.*

(Continued)

*Primary Examiner* — Shengjun Wang
(74) *Attorney, Agent, or Firm* — Saul Ewing Arnstein & Lehr LLP; Kathryn Doyle; Domingos J. Silva

(57) ABSTRACT

The present invention relates generally to compositions and methods for treating diseases and disorders caused by herpes simplex virus type 1, including herpes simplex labialis or herpes esophagitis, in a subject. In certain embodiments, the compositions of the invention comprise an ATM inhibitor and an anti-herpetic agent. In other embodiments, the compositions comprise a Chk2 inhibitor and an anti-herpetic agent. In yet other embodiments, the compositions comprise a Chk2 inhibitor and an ATM inhibitor, and optionally an anti-herpetic agent.

2 Claims, 14 Drawing Sheets

(51) Int. Cl.
*A61K 31/5377* (2006.01)
*A61K 31/4184* (2006.01)
*A61K 31/00* (2006.01)

(58) Field of Classification Search
USPC .......................................... 514/236.8, 263.3
See application file for complete search history.

(56) References Cited

OTHER PUBLICATIONS

Alekseev et al. "Novel Therapies for Herpes simplex Keratitis," ARVO Annual Meeting Abstract and Search and Program Planner, May 2011, vol. 2011, pp. 6703.*

Alekseev, et al., "Ex vivo organotypic corneal model of acute epithelial herpes simplex virus type I infection", J Vis Exp. (69): e3631, Nov. 3, 2012, 1-4.

Alekseev, et al., "Inhibition of ataxia telangiectasia mutated (ATM) kinase suppresses herpes simplex virus type 1 (HSV-1) keratitis", Invest Ophthalmol Vis Sci. 55(2), Feb. 3, 2014, 706-715.

Alekseev, et al., "Nonthermal Dielectric Barrier Discharge (DBD) Plasma Suppresses Herpes Simplex Virus Type 1 (HSV-1) Replication in Corneal Epithelium", Transl Vis Sci Technol. 3(2): Article 2, Mar. 27, 2014, 1-14.

Farooq, et al., "Herpes Simplex Epithelial and Stromal Keratitis: An Epidemiologic Update", Surv Ophthalmol.57(5), Sep. 2012, 448-462.

Alekseev, et al., Novel Therapies for Herpes Simplex Keratitis, Drexel University College of Medicine, Poster ,May 1, 2011.

Alekseev, et al., Targeting Host Genes for the Treatment of Herpes Simplex Keratitis, Drexel University College of Medicine, Poster ,Sep. 30, 2011.

Alekseev, et al., Targeting Host Kinases for the Treatment of Herpes Simplex Keratitis, Drexel University College of Medicine, Poster ,Oct. 10, 2012.

Carmine, et al., Trifluridine: a review of its antiviral activity and therapeutic use in the topical treatment of viral eye infections, Drugs. 23(5) ,1982 ,329-353.

Lester, et al., Herpes simplex virus 1 ICP4 forms complexes with TFIID and mediator in virus-infected cells, Journal of Virology 85(12) ,Jun. 2011 ,5733-5744.

Moody, et al., Human papillomaviruses activate the ATM DNA damage pathway for viral genome amplification upon differentiation, PLoS Pathog. 5(10) ,Oct. 2009 ,1-13.

Ohashi, et al., Reatment of herpetic keratitis with acyclovir: benefits and problems, Ophthalmologica. 211 Suppl 1 ,1997 ,29-32.

Yamamoto, et al., Activation of H2AX and ATM in varicella-zoster virus (VZV)-infected cells is associated with expression of specific VZV genes, Virology, 452-453 ,2014 ,52-58.

* cited by examiner

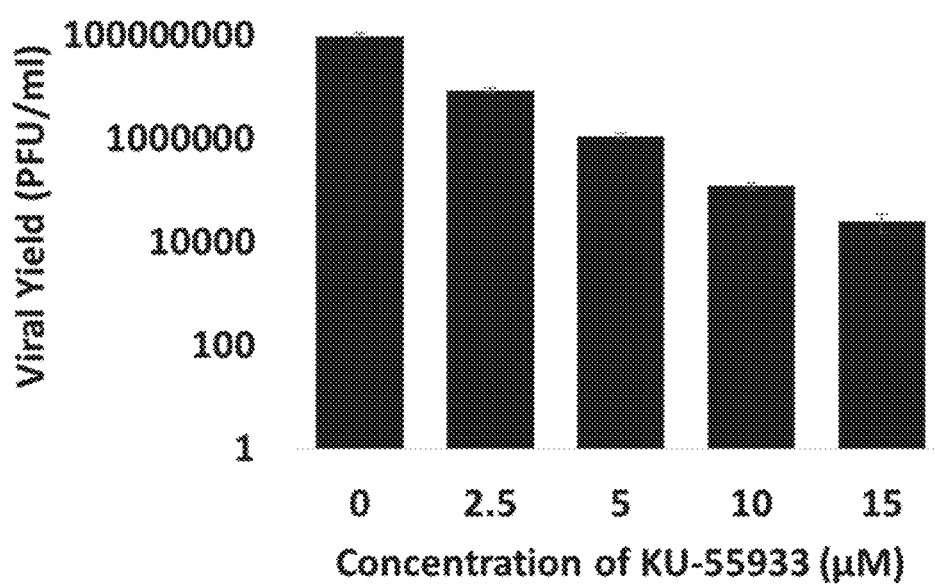

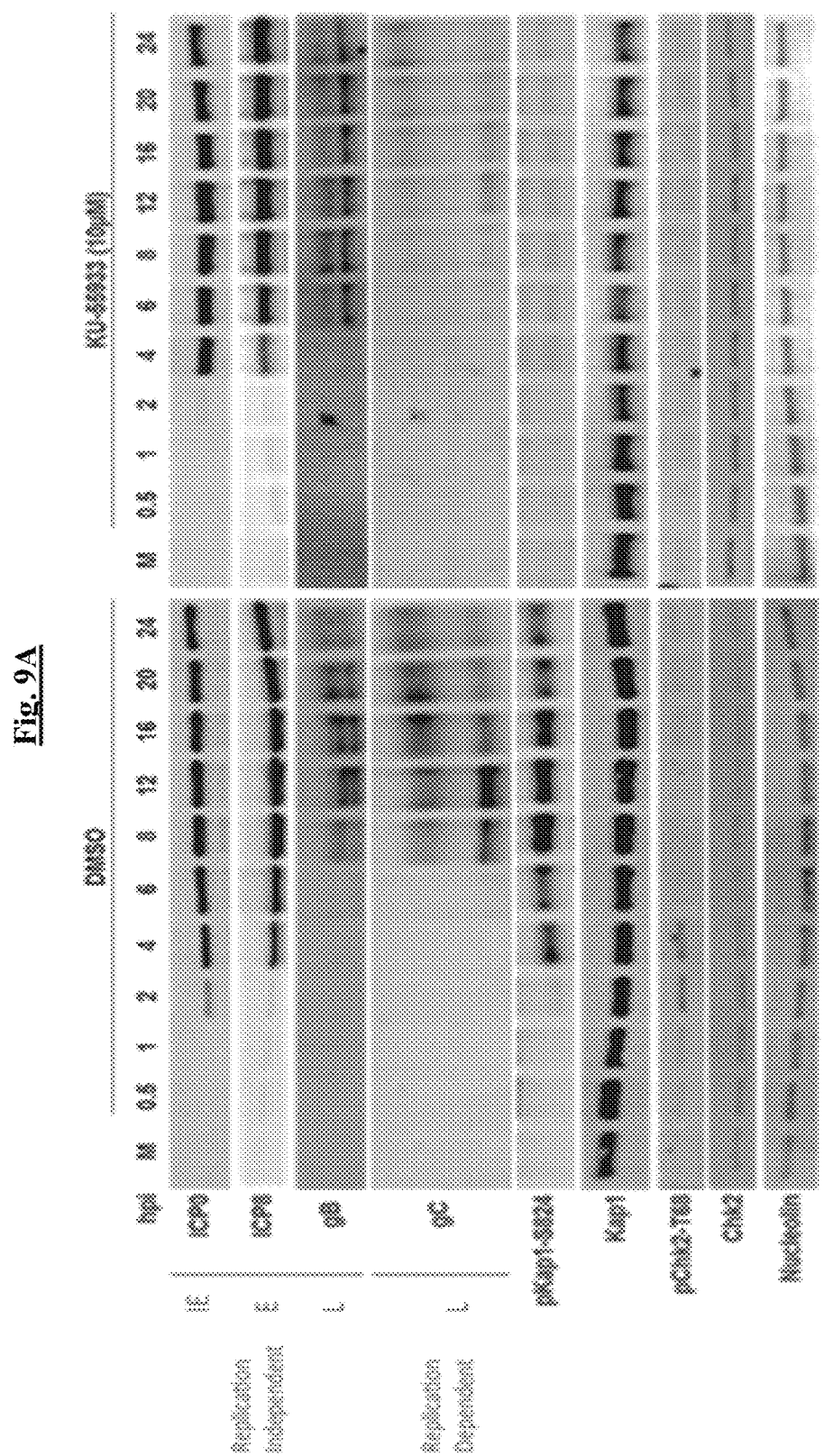

* Inoculated

\* P < 0.05
\*\* P < 0.01

| Score | Symptoms |
|---|---|
| 0 | Normal |
| 1 | White lesions |
| 2 | White lesions + redness surrounding lesion |
| 3 | Small Ulceration |
| 4 | Ulceration + matting of hair |
| 5 | Severe Ulceration and/or CNS |

COMPOSITIONS USEFUL FOR TREATING HERPES SIMPLEX LABIALIS AND/OR HERPES ESOPHAGITIS, AND METHODS USING SAME

CROSS-REFERENCE TO RELATED APPLICATIONS

The present application claims priority to U.S. Provisional Application No. 62/055,994, filed Sep. 26, 2014, the disclosure of which is incorporated herein by reference in its entirety.

BACKGROUND OF THE INVENTION

Herpes simplex labialis (also referred to as herpes labialis, cold sore, fever blister, recurrent herpes labialis, or orolabial herpes) is an infection on epithelial cells of the oral mucosal epithelium (generally including the lip). Herpes labialis infection takes place when the herpes simplex virus comes into contact with oral mucosal tissue or abraded skin of the mouth. An outbreak typically causes small painful blisters or sores on or around the mouth, usually along with fever, headache, or body aches. The sores typically heal within 2-3 weeks, but the herpes virus remains dormant in the facial nerves, following orofacial infection. Viral reactivation may be triggered by stressors such as UV light, fever, psychological stress, or local tissue trauma. In symptomatic patients, the virus is periodically reactivated to create sores in the same area of the mouth or face affected by the original infection. Rare reinfections occur inside the mouth (intraoral HSV stomatitis) affecting the gums, alveolar ridge, hard palate, and the back of the tongue, possibly accompanied by herpes labialis. In asymptomatic patients, viral shedding may still take place.

Infection by the type 1 strain of herpes simplex virus (HSV-1) is most common in herpes simplex labialis, with HSV-2 strain implicated in 10-15% of oral infections. Once the virus has entered the body, it moves from the mouth to the central nervous system, where it remains latent. In approximately one-third of people, the virus can reactivate to cause disease. When reactivation occurs, the virus travels down the nerves to the skin, where it may cause blisters (cold sores) around the lips, in the mouth or, in about 10% of cases, on the nose, chin, or 1777726.2 cheeks. Cold sore outbreaks may be influenced by stress, menstruation, sunlight, sunburn, fever, dehydration, or local skin trauma. Surgical procedures such as dental or neural surgery, lip tattooing, or dermabrasion are also common triggers.

Herpes esophagitis is a viral infection of the esophagus caused by HSV. While the disease most often occurs in immunocompromised patients (including post-chemotherapy, immunosuppression with organ transplants and in AIDS), herpes esophagitis can also occur in immunocompetent individuals. Patients experience odynophagia (painful swallowing) and dysphagia. Other symptoms can include food impaction, hiccups, weight loss, fever, and on rare occasions upper gastrointestinal bleeding and tracheoesophageal fistula.

The discovery of acyclovir revolutionized the way HSV-1 is treated, and the commonly administered drugs to treat herpes labialis and herpes esophagitis (such as famciclovir and valacyclovir) are derived from this compound. Such drugs are highly effective at treating HSV-1 maladies. However, relying on drugs that share a common mechanism of action introduces a major risk of drug resistance. Drug resistant strains of HSV-1 exist predominantly in the immunocompromised population, because the immune system normally promotes HSV-1 latency in the trigeminal ganglion and is instrumental in clearing the epithelial disease. For the roughly 5% of HIV-positive patients and 4-10% of stem cell recipients that harbor drug resistant HSV-1 strains, the only therapeutic options for treating HSV-1 are highly toxic and not nearly effective as acyclovir compounds. Two main resistance mechanisms to acyclovir-like compounds are known: at the thymidine kinase (TK) stage and at the DNA polymerase stage. Resistance through mutation of the TK gene is seen for drugs that require activation by the viral TK (e.g., acyclovir, ganciclovir, idoxuridine), but some resistant DNA polymerase mutants have also been reported. Cross-resistance between nucleoside analogue drugs further complicates the problem, highlighting the need for development of novel antiviral therapies.

HSV-1 interacts with host molecular machinery to optimize various aspects of the cellular environment for its own replication. The virus controls fundamental cellular functions, such as transcription, translation, cell cycle, autophagy, apoptosis, nuclear architecture, and antigen presentation. Among the host pathways hijacked by HSV-1 is the DNA damage response (DDR), which is a complex network of proteins responsible for the maintenance of genomic integrity of the cell. Sensor proteins of the DDR respond to DNA lesions and promote their repair by facilitating the assembly of repair proteins at the damaged DNA loci. Simultaneously, the DDR induces temporary cell cycle arrest to prevent the lesion from being passed on to the daughter cells. The DDR also induces transcriptional changes to optimize the cellular response to the incurred lesion. In the case of overwhelming or irreparable damage, the DDR promotes apoptosis of the affected cell. Three main sensor kinases serve as the apical proteins in the DDR: ATM (ataxia telangiectasia mutated), ATR (ataxia telangiectasia and Rad3 related), and DNA-PK (DNA-dependent protein kinase).

There is a need in the art for improved compositions and methods for the treatment of herpes simplex labialis. There is a further need in the art for improved compositions and methods for the treatment of herpes esophagitis. The present invention satisfies these unmet needs.

BRIEF SUMMARY OF THE INVENTION

The invention provides a composition comprising an anti-herpetic agent and at least one inhibitor selected from the group consisting of an ATM inhibitor, a Chk2 inhibitor, and a salt, solvate or N-oxide thereof. The invention further provides a method of treating or preventing a HSV-1 infection in a subject in need thereof. The invention further provides a method of treating or preventing a HSV-1 infection in a subject in need thereof, wherein the infection is caused by a drug-resistant HSV-1 strain. The invention further provides a kit for treating, ameliorating or preventing a HSV-1 infection in a subject in need thereof.

In certain embodiments, the composition treats or prevents a HSV-1 infection in a subject in need thereof. In other embodiments, the HSV-1 infection comprises at least one selected from the group consisting of herpes simplex labialis and herpes esophagitis.

In certain embodiments, the ATM inhibitor is at least one selected from the group consisting of a nucleic acid, siRNA, antisense nucleic acid, ribozyme, peptide, small molecule, antagonist, aptamer, and peptidomimetic.

In certain embodiments, the Chk2 inhibitor is at least one selected from the group consisting of a nucleic acid, siRNA, antisense nucleic acid, ribozyme, peptide, small molecule, antagonist, aptamer, and peptidomimetic.

In certain embodiments, the small molecule is at least one selected from the group consisting of caffeine, wortmannin, chloroquine, CP-466722, KU-55933, KU-59403, KU-60019, and a salt, N-oxide or solvate thereof. In other embodiments, the small molecule is at least one selected from the group consisting of Chk2 inhibitor II, SC-203885, NSC-109555, and a salt, N-oxide or solvate thereof.

In certain embodiments, the anti-herpetic agent is at least one selected from the group consisting of acyclovir, famciclovir, penciclovir, valacyclovir, acyclovir, trifluridine, penciclovir and valacyclovir.

In certain embodiments, the method comprises administering to the subject an effective amount of an anti-herpetic agent and an effective amount of at least one inhibitor selected from the group consisting of an ATM inhibitor and a Chk2 inhibitor, whereby the HSV-1 infection is treated or prevented in the subject. In other embodiments, the HSV-1 infection comprises at least one selected from the group consisting of herpes simplex labialis and herpes esophagitis.

In certain embodiments, the at least one inhibitor and the anti-herpetic agent are co-administered to the subject. In other embodiments, the at least one inhibitor and the anti-herpetic agent are co-formulated In certain embodiments, administration of the inhibitor to the subject reduces the amount of the anti-herpetic agent required to be administered to the subject to obtain the same therapeutic benefit obtained when the effective dose of the anti-herpetic agent in the absence of the inhibitor is administered to the subject.

In certain embodiments, the subject experiences less frequent or less severe side effects of the anti-herpetic agent, as compared to when the effective dose of the anti-herpetic agent in the absence of the inhibitor is administered to the subject.

In certain embodiments, development of resistance to the anti-herpetic agent is prevented or minimized in the subject, as compared to when the effective dose of the anti-herpetic agent in the absence of the inhibitor is administered to the subject.

In certain embodiments, the method comprises administering to the subject an effective amount of at least one inhibitor selected from the group consisting of an ATM inhibitor and a Chk2 inhibitor, wherein the subject is optionally further administered an effective amount of an anti-herpetic agent. In other embodiments, administration of the at least one inhibitor treats or prevents the HSV-1 infection in the subject. In yet other embodiments, the HSV-1 infection comprises at least one selected from the group consisting of herpes simplex labialis and herpes esophagitis.

In certain embodiments, the drug-resistant HSV-1 strain has a TK mutation. In other embodiments, the strain is resistant to at least one selected from the group consisting of acyclovir, famciclovir, penciclovir, valacyclovir, acyclovir, trifluridine, penciclovir and valacyclovir.

In certain embodiments, the inhibitor and/or anti-herpetic agent is administered to the subject by a topical, transdermal, oral or buccal route. In yet other embodiments, the inhibitor and/or anti-herpetic agent is administered to the subject by at least one route selected from aerosol, ophthalmic, inhalational, oral, nasal, rectal, parenteral, sublingual, transdermal, transmucosal (e.g., sublingual, lingual, (trans) buccal, (trans)urethral, vaginal (e.g., trans- and perivaginally), (intra)nasal, and (trans)rectal), intravesical, intracranial, intracerebroventricular, intrapulmonary, intraduodenal, intragastrical, intrathecal, subcutaneous, intramuscular, epidural, intradermal, intra-arterial, intravenous, intrabronchial, inhalation, and topical.

In certain embodiments, the subject is a mammal. In other embodiments, the mammal is a human.

In certain embodiments, the kit comprises at least one inhibitor selected from the group consisting of an ATM inhibitor and a Chk2 inhibitor. In other embodiments, the kit further comprises an applicator; and an instructional material for the use of the kit, wherein the instruction material comprises instructions for treating, ameliorating or preventing a HSV-1 infection in a subject in need thereof. In yet other embodiments, the HSV-1 infection comprises at least one selected from the group consisting of herpes simplex labialis and herpes esophagitis. In yet other embodiments, the kit further comprises an anti-herpetic agent.

BRIEF DESCRIPTION OF THE DRAWINGS

The following detailed description of specific embodiments of the invention will be better understood when read in conjunction with the appended drawings. For the purpose of illustrating the invention, specific embodiments are shown in the drawings. It should be understood, however, that the invention is not limited to the precise arrangements and instrumentalities of the embodiments shown in the drawings.

FIGS. 7A-7C comprise a set of graphs demonstrating that KU-55933 (FIGS. 7A and 7C) and Chk2 Inhibitor II (FIG. 7B) reduce HSV-1 genome copy numbers and viral yield in a dose-dependent manner (MOI=0.1, analysis at 20 hours post infection).

FIGS. 9A-9E comprise a set of images and graphs illustrating the KU-55933 and Chk2 Inhibitor II prevent the transcription and synthesis of the viral true-late factor gC while having minimal effect on the viral immediate early factor ICP0, early factors ICP8 and thymidine kinase, and leaky-late factor gB. FIGS. 9A-9B: MOI=5; FIGS. 9C-9E: MOI=0.1.

DETAILED DESCRIPTION OF THE INVENTION

Figure 1:
FIG. 1 comprises an image illustrating a lip sore associated with herpes labialis.
Figure 2:
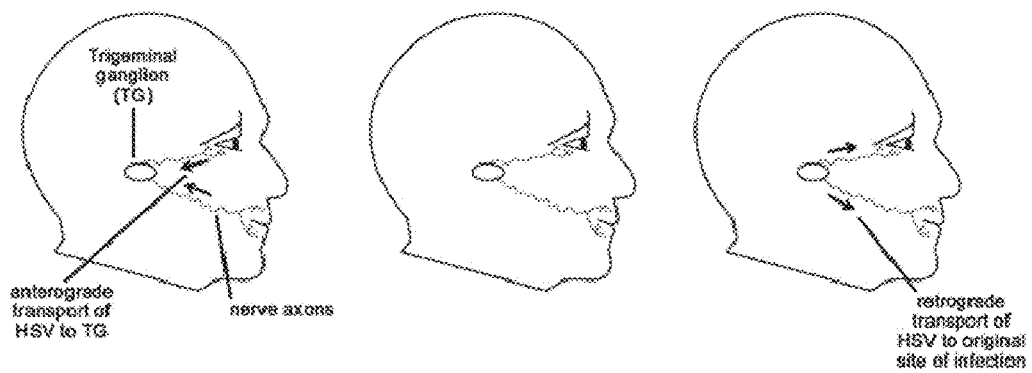
FIG. 2 comprises an illustration of the acute, latent and reactivation stages of HSV-1 infection associated with herpes labialis (left to right).
Figure 3:
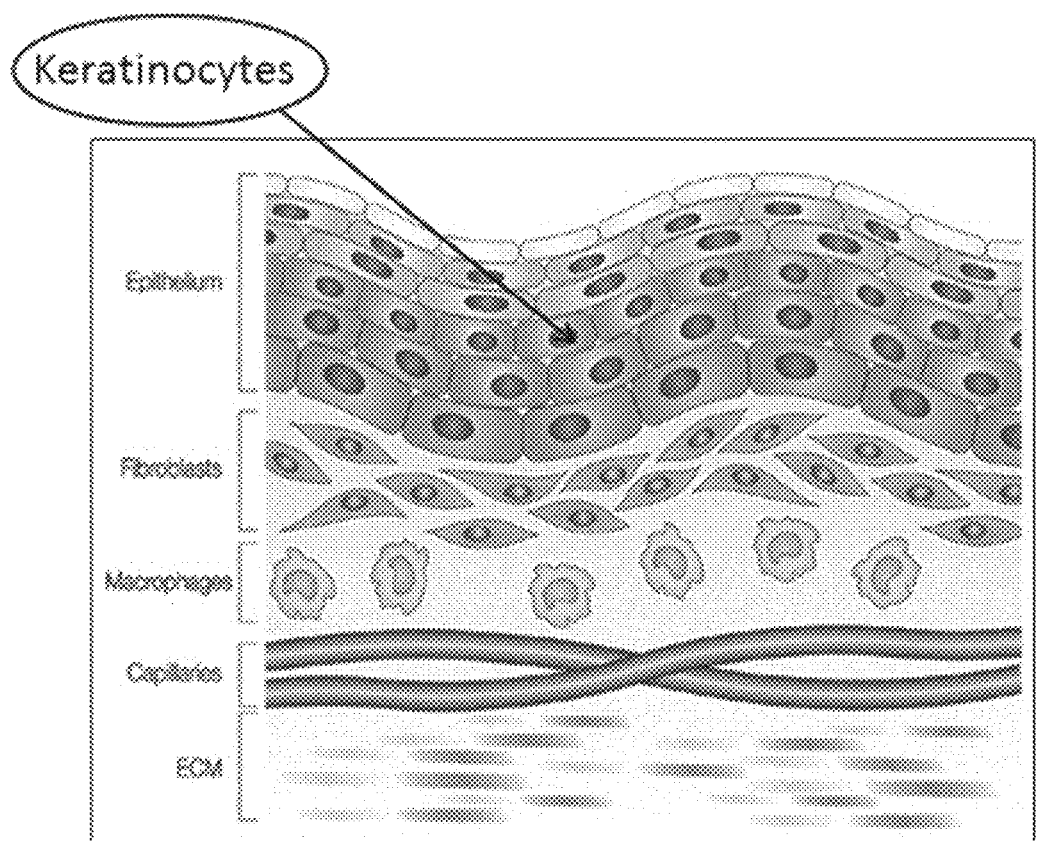
FIG. 3 is a schematic illustration of keratinocytes (such as OKF6/Tert2) derived from normal oral mucosal epithelium. OKF6/Tert2 cells are immortalized with telomerase.

The present invention relates generally to compositions and methods for treating diseases and disorders caused by herpes simplex virus type 1, including herpes simplex labialis and/or herpes esophagitis, in a subject. In one aspect, the present invention provides a composition for treating herpes simplex labialis in a subject. In another aspect, the present invention provides a composition for treating herpes esophagitis in a subject. In certain embodiments, the compositions of the invention comprise an ATM inhibitor. In other embodiments, the compositions of the invention comprise a Chk2 inhibitor. In yet other embodiments, the compositions of the invention comprise an ATM inhibitor and an anti-herpetic agent. In yet other embodiments, the compositions of the invention comprise a Chk2 inhibitor and an anti-herpetic agent. In yet other embodiments, the compositions of the invention comprise a Chk2 inhibitor and an ATM inhibitor, and optionally an anti-herpetic agent.

In one aspect, the present invention provides a method of treating or preventing herpes simplex labialis in a subject in need thereof. In another aspect, the present invention provides a method of treating or preventing herpes esophagitis in a subject in need thereof.

In certain embodiments, the method comprises administering to the subject an effective amount of an ATM inhibitor. In other embodiments, the method comprises administering to the subject an effective amount of a Chk2 inhibitor. In yet other embodiments, the method comprises administering to the subject an effective amount of a composition comprising an ATM inhibitor and an anti-herpetic agent. In yet other embodiments, the method comprises administering to the subject an effective amount of a composition comprising a Chk2 inhibitor and an anti-herpetic agent. In yet other embodiments, the method comprises administering to the subject an effective amount of a composition comprising an ATM inhibitor, a Chk2 inhibitor and optionally an anti-herpetic agent. In yet other embodiments, the method comprises administering to the subject an effective amount of an ATM inhibitor and an effective amount of an anti-herpetic agent. In yet other embodiments, the method comprises administering to the subject an effective amount of a Chk2 inhibitor and an effective amount of an anti-herpetic agent. In yet other embodiments, the method comprises administering to the subject an effective amount of a Chk2 inhibitor, an effective amount of an ATM inhibitor and optionally an effective amount of an anti-herpetic agent.

In certain embodiments, administration of an ATM inhibitor reduces the effective amount of the anti-herpetic agent required to be administered to the subject to obtain the same therapeutic benefit. In other embodiments, administration of a Chk2 inhibitor reduces the effective amount of the anti-herpetic agent required to be administered to the subject to obtain the same therapeutic benefit. In yet other embodiments, the reduced effective amount of the anti-herpetic agent required to be administered to the subject to obtain the same therapeutic benefit results in a reduced frequency or severity of side effects due to the anti-herpetic agent experienced by the subject. In yet other embodiments, the infection is caused by a drug-resistant HSV-1 strain. In yet other embodiments, the drug-resistant HSV-1 strain has a TK mutation. In yet other embodiments, the strain is resistant to at least one selected from the group consisting of acyclovir, famciclovir, penciclovir, valacyclovir, acyclovir, trifluridine, penciclovir and valacyclovir.

As demonstrated herein, ATM is a significant participant in HSV-1 infection. ATM is rapidly activated in response to infection in an oral epithelial cell, and inhibition of its kinase activity with a small molecule inhibitor, KU-55933, greatly reduces replication of the virus.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are described.

Generally, the nomenclature used herein and the laboratory procedures in cell culture, molecular genetics, organic chemistry, virology, and nucleic acid chemistry and hybridization are those well-known and commonly employed in the art. The nomenclature used herein and the laboratory procedures used in analytical chemistry described below are those well-known and commonly employed in the art. Standard techniques or modifications thereof, are used for chemical syntheses and chemical analyses.

Standard techniques are used for nucleic acid and protein isolation. The techniques and procedures are generally performed according to conventional methods in the art and various general references (e.g., Sambrook and Russell, 2012, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

As used herein, each of the following terms has the meaning associated with it in this section.

As used herein, the articles "a" and "an" refer to one or to more than one (i.e., to at least one) of the grammatical object of the article. By way of example, "an element" means one element or more than one element.

As used herein, "about" when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, a disease or disorder is "alleviated" if the severity or frequency of at least one sign or symptom of the disease or disorder experienced by a patient is reduced.

As used herein, the term "analog" or "analogue" or "derivative" is meant to refer to a chemical compound or molecule made from a parent compound or molecule by one or more chemical reactions. As such, an analog can be a structure having a structure similar to that of the small molecule inhibitors described herein or can be based on a scaffold of a small molecule inhibitor described herein, but differing from it in respect to certain components or structural makeup, which may have a similar or opposite action metabolically. An analog or derivative of any of a small molecule inhibitor in accordance with the present invention can be used within the methods of the invention.

As the term is used herein, "applicator" is used to identify any device including, but not limited to, a hypodermic syringe, pipette, nebulizer, vaporizer and the like, for administering the compounds and compositions used in the practice of the invention.

As used herein, the term "ATM" kinase refers to ataxia telangiectasia mutated kinase.

As used herein, the term "ATR" kinase refers to ataxia telangiectasia and Rad3 related kinase.

As used herein, the phrase "ATM inhibitor" or "inhibitor of ATM" refers to a composition or compound that inhibits ATM activity, either directly or indirectly, using any method known to the skilled artisan. An ATM inhibitor may be any type of compound, including but not limited to, a nucleic acid, peptide, antibody, small molecule, antagonist, aptamer, or peptidomimetic.

As used herein, the phrase "Chk2 inhibitor" or "inhibitor of Chk2" refers to a composition or compound that inhibits Chk2 activity, either directly or indirectly, using any method known to the skilled artisan. A Chk2 inhibitor may be any type of compound, including but not limited to, a nucleic acid, peptide, antibody, small molecule, antagonist, aptamer, or peptidomimetic.

As used herein, the phrase "Chk2 inhibitor II" refers to 2-(4-(4-chlorophenoxy)phenyl)-1H-benzimidazole-5-carboxamide, or a salt, N-oxide or solvate thereof:

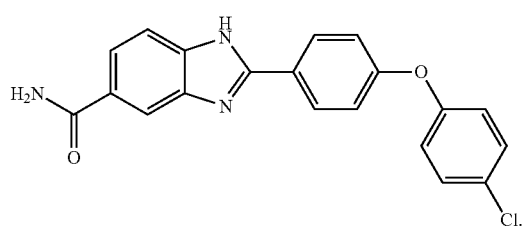

Chk2 inhibitor II

As used herein, the term "chloroquine" refers to $N^4$-(7-chloro-4-quinolinyl)-N1,N1-diethyl-1,4-pentanediamine, or a salt, N-oxide or solvate thereof:

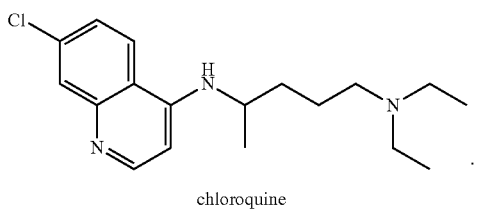 [SMILES: CCN(CC)CCCC(C)Nc1ccnc2cc(Cl)ccc12]

chloroquine

As used herein, the term "CP-466722" or "CP466722" refers to 2-(6,7-dimethoxyquinazolin-4-yl)-5-(pyridin-2-yl)-2H-1,2,4-triazol-3-amine, or a salt, N-oxide or solvate thereof:

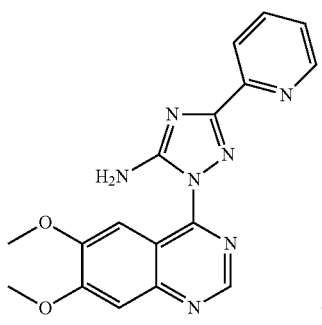

CP-466722

As used herein, the term "container" includes any receptacle for holding the pharmaceutical composition. For example, in certain embodiments, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well-known in the art. It should be understood that the instructions for use of the pharmaceutical composition may be contained on the packaging containing the pharmaceutical composition, and as such the instructions form an increased functional relationship to the packaged product. However, it should be understood that the instructions can contain information pertaining to the compound's ability to perform its intended function, e.g., treating, ameliorating, or preventing HSV-1 infection in a subject.

As used herein, the term "DDR" refers to DNA damage response.

As used herein, a "disease" is a state of health of an animal, such as a human, wherein the animal cannot maintain homeostasis, and wherein if the disease is not ameliorated then the animal's health continues to deteriorate.

As used herein, a "disorder" in an animal, such as a human, is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "DNA-PK" refers to DNA-dependent protein kinase.

As used herein, the term "dpi" refers to days post-infection.

As used herein, the terms "effective amount" and "pharmaceutically effective amount" and "therapeutically effective amount" refer to an amount of an agent to provide the desired biological or therapeutic result. That result can be reduction and/or alleviation of the signs, symptoms, or causes of a disease or disorder, or any other desired alteration of a biological system. An appropriate effective amount in any individual case may be determined by one of ordinary skill in the art using routine experimentation.

As used herein, the term "endogenous" refers to any material from or produced inside an organism, cell, tissue or system.

As used herein, the term "exogenous" refers to any material introduced from or produced outside an organism, cell, tissue or system.

As used herein, the term "expression" is defined as the transcription and/or translation of a particular nucleotide sequence driven by its promoter.

As used herein, the term "HSV-1" refers to herpes simplex virus type 1.

As used herein, the term "HSV-2" refers to herpes simplex virus type 2.

As used herein, the terms "inhibit" and "inhibition" mean to reduce a molecule, a reaction, an interaction, a gene, an mRNA, and/or a protein's expression, stability, function or activity by a measurable amount or to prevent entirely. "Inhibitors" are compounds that, e.g., bind to, partially or totally block stimulation, decrease, prevent, delay activation, inactivate, desensitize, or down regulate a protein, a gene, and an mRNA stability, expression, function and activity, e.g., antagonists.

"Instructional material," as that term is used herein, includes a publication, a recording, a diagram, or any other medium of expression which can be used to communicate the usefulness of a composition of the invention in a kit. The instructional material of the kit may, for example, be affixed to a container that contains a composition of the invention or be shipped together with a container which contains a composition. Alternatively, the instructional material may be shipped separately from the container with the intention that the recipient uses the instructional material and a composition cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

As used herein, the term "KU-55933" or "KU55933" refers to 2-(morpholin-4-yl)-6-(thianthren-1-yl)-pyran-4-one, or a solvate, salt, N-oxide, or prodrug thereof:

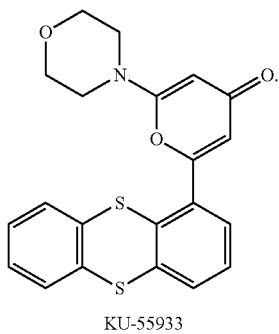 [SMILES: O=c1cc(-c2cccc3c2Sc2ccccc2S3)oc(N2CCOCC2)c1]

KU-55933

As used herein, the term "KU-59403" or "KU59403" refers to 3-(4-methyl piperazin-1-yl)-N-(6-(6-morpholino-4-oxo-4H-pyran-2-yl)thianthren-2-yl)propanamide, or a solvate, salt, N-oxide, or prodrug thereof:

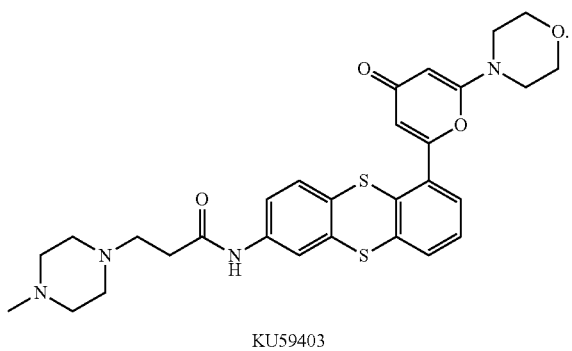 [SMILES: CN1CCN(CCC(=O)Nc2ccc3c(c2)Sc2cccc(-c4cc(=O)cc(N5CCOCC5)o4)c2S3)CC1]

KU59403

As used herein, the term "KU-60019" or "KU60019" refers to 2-(2,6-dimethylmorpholin-4-yl)-N-(5-(6-morpholin-4-yl-4-oxo-4H-pyran-2-yl)-9H-thioxanthen-2-yl)acetamide, or a solvate, salt, N-oxide, or prodrug thereof:

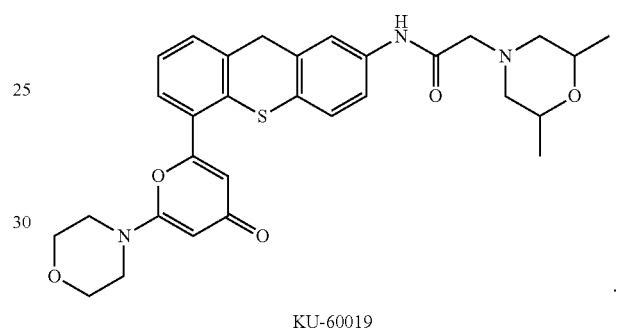

KU-60019

As used herein, the term "NSC-109555" or NSC 109555" refers to 4,4'-diacetyldiphenylurea bis(guanylhydrazone) or a solvate, salt, N-oxide, or prodrug thereof:

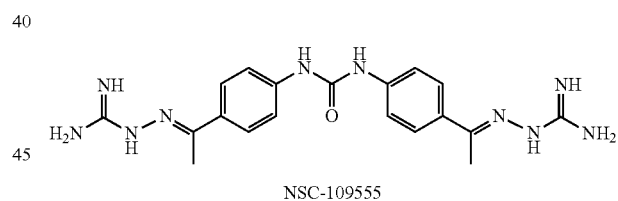

NSC-109555

As used herein, the term "PAA" refers to phosphonoacetic acid, or a salt or solvate thereof.

As used herein, the term "pharmaceutically acceptable" refers to a material, such as a carrier or diluent, which does not abrogate the biological activity or properties of the composition, and is relatively non-toxic, i.e., the material may be administered to an individual without causing undesirable biological effects or interacting in a deleterious manner with any of the components of the composition in which it is contained.

As used herein, a "pharmaceutically acceptable carrier" means a pharmaceutically acceptable material, composition or carrier, such as a liquid or solid filler, diluent, excipient, solvent or encapsulating material, involved in carrying or transporting a compound(s) of the invention within or to the subject such that it can perform its intended function. Typically, such compounds are carried or transported from one organ, or portion of the body, to another organ, or portion of the body. Each carrier must be "acceptable" in the sense of being compatible with the other ingredients of the formulation, and not injurious to the patient. Some examples of materials that can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. As used herein "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds can also be incorporated into the compositions.

As used herein, the term "pharmaceutical composition" or "composition" refers to a mixture of at least one compound useful within the invention with other chemical components, such as carriers, stabilizers, diluents, dispersing agents, suspending agents, thickening agents, and/or excipients. The pharmaceutical composition facilitates administration of the compound to an organism. The compositions of the present invention may be administered to a subject by any available routes. Routes of administration of any of the compositions of the invention include aerosol, ophthalmic, inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intracranial, intracerebroventricular, intrapulmonary, intraduodenal, intragastrical, intrathecal, subcutaneous, intramuscular, epidural, intradermal, intra-arterial, intravenous, intrabronchial, inhalation, and topical administration. In certain embodiments, the administration comprises topical administration.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

As used herein, a viral strain is "resistant" to an antiviral agent if the minimum concentration necessary to inhibit the growth and/or kill the strain is higher than the average minimum concentration that inhibits the growth and/or kills other strains of the same virus. In certain embodiments, the minimum concentration of the antiviral agent necessary to inhibit the growth and/or kill the resistant strain is at least about 2 times higher, about 4 times higher, about 8 times higher, about 16 times higher, about 32 times higher, about 64 times higher, about 128 times higher, about 256 times higher, about 512 times higher, about 1,024 times higher, or about 2,048 times higher, about 10,000 times higher, or about 100,000 times higher than the average minimum concentration of the antiviral agent that inhibits the growth and/or kills other strains of the same virus.

As used herein, the term "SC-203885" refers to (Z)-5-(2-amino-5-oxo-1,5-dihydro-4H-imidazol-4-ylidene)-3,4,5,5a,10,10a-hexahydroazepino[3,4-b]indol-1(2H)-one, or a solvate, salt, N-oxide, or prodrug thereof:

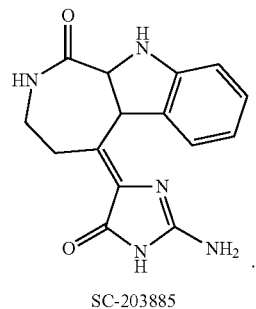 [SMILES: NC1=N/C(=C2/CCNC(=O)C3Nc4ccccc4C23)C(=O)N1]

SC-203885

By the term "specifically bind" or "specifically binds" as used herein is meant that a first molecule (e.g., an antibody) preferentially binds to a second molecule (e.g., a particular antigenic epitope), but does not necessarily bind only to that second molecule.

As used herein, the term "subject" or "patient" or "individual" includes humans and other animals, particularly mammals, and other organisms. Thus the methods are applicable to both human therapy and veterinary applications. In a specific embodiment, the patient is a mammal, and in certain embodiments the patient is human.

As used herein, the term "TK" refers to thymidine kinase.

As used herein, the terms "treat," "treating," and "treatment," refer to therapeutic or preventative measures described herein. The methods of "treatment" employ administration to a subject, in need of such treatment, a composition of the invention, for example, a subject afflicted a disease or disorder, or a subject who ultimately may acquire such a disease or disorder, in order to prevent, cure, delay, reduce the severity of, or ameliorate one or more symptoms of the disorder or recurring disorder, or in order to prolong the survival of a subject beyond that expected in the absence of such treatment.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates generally to compositions and methods for treating diseases and disorders caused by herpes simplex virus type 1, including herpes simplex labialis and/or herpes esophagitis, in a subject. In one aspect, the present invention provides a composition for treating herpes simplex labialis in a subject. In another aspect, the present invention provides a composition for treating herpes esophagitis in a subject. In certain embodiments, the compositions of the invention comprise an ATM inhibitor. In other embodiments, the compositions comprise a Chk2 inhibitor. In yet other embodiments, the compositions of the invention comprise an ATM inhibitor and an anti-herpetic agent. In yet other embodiments, the compositions comprise a Chk2 inhibitor and an anti-herpetic agent. In yet other embodiments, the compositions comprise a Chk2 inhibitor and an ATM inhibitor, and optionally an anti-herpetic agent.

In one aspect, the present invention provides a method of treating or preventing herpes simplex labialis in a subject in need thereof. In another aspect, the present invention provides a method of treating or preventing herpes esophagitis in a subject in need thereof.

In certain embodiments, the method comprises administering to the subject an effective amount of an ATM inhibitor. In other embodiments, the method comprises administering to the subject an effective amount of a Chk2 inhibitor. In yet other embodiments, the method comprises administering to the subject an effective amount of a composition comprising an ATM inhibitor and an anti-herpetic agent. In yet other embodiments, the method comprises administering to the subject an effective amount of a composition comprising a Chk2 inhibitor and an anti-herpetic agent. In yet other embodiments, the method comprises administering to the subject an effective amount of a composition comprising an ATM inhibitor, a Chk2 inhibitor and optionally an anti-herpetic agent. In yet other embodiments, the method comprises administering to the subject an effective amount of an ATM inhibitor and an effective amount of an anti-herpetic agent. In yet other embodiments, the method comprises administering to the subject an effective amount of a Chk2 inhibitor and an effective amount of an anti-herpetic agent. In yet other embodiments, the method comprises administering to the subject an effective amount of a Chk2 inhibitor, an effective amount of an ATM inhibitor and optionally an effective amount of an anti-herpetic agent.

In certain embodiments, administration of an ATM inhibitor reduces the effective amount of the anti-herpetic agent required to be administered to the subject to obtain the same therapeutic benefit. In other embodiments, administration of a Chk2 inhibitor reduces the effective amount of the anti-herpetic agent required to be administered to the subject to obtain the same therapeutic benefit. In yet other embodiments, the reduced effective amount of the anti-herpetic agent required to be administered to the subject to obtain the same therapeutic benefit results in a reduced frequency or severity of side effects due to the anti-herpetic agent experienced by the subject. In yet other embodiments, the infection is caused by a drug-resistant HSV-1 strain. In yet other embodiments, the drug-resistant HSV-1 strain has a TK mutation. In yet other embodiments, the strain is resistant to at least one selected from the group consisting of acyclovir, famciclovir, penciclovir, valacyclovir, acyclovir, trifluridine, penciclovir and valacyclovir.

In certain embodiments, the ATM inhibitor is at least one selected from the group consisting of a nucleic acid, an antisense nucleic acid, an siRNA, a ribozyme, an shRNA, a peptide, an antibody, a small molecule, an antagonist, an aptamer, or a peptidomimetic that reduces the expression or activity of ATM. In other embodiments, the ATM inhibitor is selected from the group consisting of caffeine, wortmannin, chloroquine, CP-466722, KU-55933, KU-59403 and KU-60019, a salt or solvate thereof, and any combinations thereof.

In certain embodiments, the Chk2 inhibitor is at least one selected from the group consisting of a nucleic acid, an antisense nucleic acid, an siRNA, a ribozyme, an shRNA, a peptide, an antibody, a small molecule, an antagonist, an aptamer, or a peptidomimetic that reduces the expression or activity of Chk2 In other embodiments, the Chk2 inhibitor is Chk2 inhibitor II, SC-203885 or NSC-109555.

In certain embodiments, the anti-herpetic agent is at least one selected from the group consisting of acyclovir, famciclovir, penciclovir, valacyclovir, acyclovir, trifluridine, penciclovir and valacyclovir.

In certain embodiments, the composition comprises a combination of inhibitors described herein. For example, in certain embodiments the composition comprises a combination of an ATM inhibitor and a Chk2 inhibitor, in combination with an optional anti-herpetic agent.

In one aspect, the present studies shed light on the concept of interfering with the host DDR in order to treat herpes simplex labialis and/herpes esophagitis infection. The traditional approach of inhibiting critical viral proteins, such as DNA polymerase, has clear limitations. Analogous to antibiotic drugs, antiviral compounds that specifically target a viral factor leave room for mutation-driven development of resistance. This is a well-recognized emerging clinical problem, particularly in immunosuppressed populations. The most common mechanism of resistance to nucleoside analogues (~95%) is mutation of the viral TK gene. By contrast, disruption of a critical virus-host interaction via inhibition of a host factor suppresses viral replication without the risk of rapid development of mutation-based resistance.

In certain embodiments of the invention, ATM inhibitors are combined with established antiviral agents in the treatment of the diseases and/or disorders contemplated herein.

Without wishing to be limited by any theory, the diversification of targeted pathways accomplished by combination therapy has the two-fold advantage of preventing resistance and allowing for a reduction in drug dosage, with a consequent attenuation of side effect severity of each individual drug.

Inhibitors

In certain embodiments, the compositions of the invention comprise an ATM inhibitor. An ATM inhibitor is any compound or molecule that reduces, inhibits, or prevents the function of ATM. For example, an ATM inhibitor is any compound or molecule that reduces ATM expression, activity, or both. In certain embodiments, an ATM inhibitor comprises at least one selected from the group consisting of a nucleic acid, an antisense nucleic acid, an siRNA, a ribozyme, an shRNA, a peptide, an antibody, a small molecule, an antagonist, an aptamer, and a peptidomimetic.

In certain embodiments, the composition of the invention comprises an Chk2 inhibitor. A Chk2 inhibitor is any compound or molecule that reduces, inhibits, or prevents the function of Chk2 For example, a Chk2 inhibitor is any compound or molecule that reduces Chk2 expression, activity, or both. In certain embodiments, a Chk2 inhibitor comprises at least one selected from the group consisting of a nucleic acid, an antisense nucleic acid, an siRNA, a ribozyme, an shRNA, a peptide, an antibody, a small molecule, an antagonist, an aptamer, and a peptidomimetic.

In certain embodiments, the compositions of the invention comprises a pharmaceutically acceptable carrier.

The compounds described herein may form salts with acids or bases, and such salts are included in the present invention. In certain embodiments, the salts are pharmaceutically acceptable salts. The term "salts" embraces addition salts of free acids or bases that are useful within the methods of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

Small Molecule Inhibitors

In certain embodiments, the inhibitor is a small molecule. When the inhibitor is a small molecule, a small molecule may be obtained using standard methods known to the skilled artisan. Such methods include chemical organic synthesis or biological means. Biological means include purification from a biological source, recombinant synthesis and in vitro translation systems, using methods well known in the art. In certain embodiments, a small molecule inhibitor of the invention comprises an organic molecule, an inorganic molecule, a biomolecule, and the like.

Combinatorial libraries of molecularly diverse chemical compounds potentially useful in treating a variety of diseases and conditions are well known in the art as are method of making the libraries. The method may use techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery vs. biased structures for lead development.

In a general method for small library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

Small molecule inhibitors of ATM are known in the art. Exemplary small molecule ATM inhibitors include, but are not limited to caffeine, wortmannin, chloroquine, CP-466722, KU-55933, KU-59403 or KU-60019. Exemplary small molecule Chk2 inhibitors include, but are not limited to Chk2 inhibitor II, SC-203885 or NSC-109555.

Where tautomeric forms may be present for any of the inhibitors described herein, each and every tautomeric form is intended to be included in the present invention, even though only one or some of the tautomeric forms may be explicitly illustrated.

The invention also includes any or all of the stereochemical forms, including any enantiomeric or diasteriomeric forms of the inhibitors described. The recitation of the structure or name herein is intended to embrace all possible stereoisomers of inhibitors depicted. All forms of the inhibitors are also embraced by the invention, such as crystalline or non-crystalline forms of the inhibitors. Compositions comprising an inhibitor of the invention are also intended, such as a composition of substantially pure inhibitor, including a specific stereochemical form thereof, or a composition comprising mixtures of inhibitors of the invention in any ratio, including two or more stereochemical forms, such as in a racemic or non-racemic mixture. In certain embodiments, the small molecule inhibitor of the invention comprises an analog or derivative of an inhibitor described herein.

In certain embodiments, the small molecules described herein are candidates for derivatization. In certain embodiments, the analogs of the small molecules described herein that have modulated potency, selectivity, and solubility are included herein and provide useful leads for drug discovery and drug development. Thus, in certain instances, during optimization new analogs are designed considering issues of drug delivery, metabolism, novelty, and safety.

In some instances, small molecule inhibitors described herein are derivatized/analogued as is well known in the art of combinatorial and medicinal chemistry. The analogs or derivatives can be prepared by adding and/or substituting functional groups at various locations. As such, the small molecules described herein can be converted into derivatives/analogs using well known chemical synthesis procedures. For example, all of the hydrogen atoms or substituents can be selectively modified to generate new analogs. Also, the linking atoms or groups can be modified into longer or shorter linkers with carbon backbones or hetero atoms. Also, the ring groups can be changed so as to have a different number of atoms in the ring and/or to include hetero atoms. Moreover, aromatics can be converted to cyclic rings, and vice versa. For example, the rings may be from 5-7 atoms, and may be homocycles or heterocycles.

In certain embodiments, the small molecule inhibitors described herein can independently be derivatized/analogued by modifying hydrogen groups independently from each other into other substituents. That is, each atom on each molecule can be independently modified with respect to the other atoms on the same molecule. Any traditional modification for producing a derivative/analog can be used. For example, the atoms and substituents can be independently comprised of hydrogen, an alkyl, aliphatic, straight chain aliphatic, aliphatic having a chain hetero atom, branched aliphatic, substituted aliphatic, cyclic aliphatic, heterocyclic aliphatic having one or more hetero atoms, aromatic, heteroaromatic, polyaromatic, polyamino acids, peptides, polypeptides, combinations thereof, halogens, halo-substituted aliphatics, and the like. Additionally, any ring group on a compound can be derivatized to increase and/or decrease ring size as well as change the backbone atoms to carbon atoms or hetero atoms.

Nucleic Acid Inhibitors

In certain embodiments, the invention includes an isolated nucleic acid. In other embodiments, the inhibitor is an siRNA, shRNA or antisense molecule, which inhibits ATM or Chk2 In certain embodiments, the nucleic acid comprises a promoter/regulatory sequence such that the nucleic acid is preferably capable of directing expression of the nucleic acid. Thus, the invention encompasses expression vectors and methods for the introduction of exogenous DNA into cells with concomitant expression of the exogenous DNA in the cells such as those described, for example, in Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York) and as described elsewhere herein.

In certain embodiments, ATM or Chk2 can be inhibited by way of inactivating and/or sequestering ATM or Chk2 As such, inhibiting the activity of ATM or Chk2 can be accomplished by using a transdominant negative mutant.

In certain embodiments, a nucleic acid is used to decrease the level of ATM or Chk2 protein. RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., 1998, Nature 391(19):306-311; Timmons et al., 1998, Nature 395:854; Montgomery et al., 1998, TIG 14 (7):255-258; David R. Engelke, Ed., RNA Interference (RNAi) Nuts & Bolts of RNAi Technology, DNA Press, Eagleville, Pa. (2003); and Gregory J. Hannon, Ed., RNAi A Guide to Gene Silencing, Cold Spring Harbor Laboratory Press, Cold Spring Harbor, N.Y. (2003). Soutschek et al. (2004, Nature 432:173-178) describe a chemical modification to siRNAs that aids in intravenous systemic delivery. Optimizing siRNAs involves consideration of overall G/C content, C/T content at the termini, $T_m$ and the nucleotide content of the 3' overhang. See, for instance, Schwartz et al., 2003, Cell, 115:199-208 and Khvorova et al., 2003, Cell 115:209-216. Therefore, the present invention also includes methods of decreasing levels of ATM or Chk2 using RNAi technology.

In another aspect, the invention includes a vector comprising an siRNA or antisense nucleic acid. Preferably, the antisense nucleic acid is capable of inhibiting the expression of a target polypeptide, wherein the target polypeptide is selected from the group consisting of ATM and Chk2 The incorporation of a desired polynucleotide into a vector and the choice of vectors is well-known in the art as described in, for example, Sambrook et al. (2012), and in Ausubel et al. (1997), and elsewhere herein.

In certain embodiments, the expression vectors described herein encode a short hairpin RNA (shRNA) inhibitor. shRNA inhibitors are well known in the art and are directed against the mRNA of a target, thereby decreasing the expression of the target. In certain embodiments, the encoded shRNA is expressed by a cell, and is then processed into siRNA. For example, in certain instances, the cell possesses native enzymes (e.g., dicer) that cleaves the shRNA to form siRNA.

The siRNA, shRNA, or antisense nucleic acid can be cloned into a number of types of vectors as described elsewhere herein. For expression of the siRNA or antisense polynucleotide, at least one module in each promoter functions to position the start site for RNA synthesis.

In order to assess the expression of the siRNA, shRNA, or antisense polynucleotide, the expression vector to be introduced into a cell can also contain either a selectable marker gene or a reporter gene or both to facilitate identification and selection of expressing cells from the population of cells sought to be transfected or infected using a viral vector. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neomycin resistance and the like.

Therefore, in another aspect, the invention relates to a vector, comprising the nucleotide sequence of the invention or the construct of the invention. The choice of the vector will depend on the host cell in which it is to be subsequently introduced. In certain embodiments, the vector of the invention is an expression vector. Suitable host cells include a wide variety of prokaryotic and eukaryotic host cells. In other embodiments, the expression vector is selected from the group consisting of a viral vector, a bacterial vector and a mammalian cell vector. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al. (2012), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

By way of illustration, the vector in which the nucleic acid sequence is introduced can be a plasmid that is or is not integrated in the genome of a host cell when it is introduced in the cell. Illustrative, non-limiting examples of vectors in which the nucleotide sequence of the invention or the gene construct of the invention can be inserted include an inducible vector for expression in eukaryote cells. The vector may be obtained by conventional methods known by persons skilled in the art (Sambrook et al., 2012). In a particular embodiment, the vector is a vector useful for transforming animal cells.

In certain embodiments, the recombinant expression vectors may also contain nucleic acid molecules which encode a peptide or peptidomimetic inhibitor of invention, described elsewhere herein.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (U.S. Pat. No. 4,683,202, U.S. Pat. No. 5,928,906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2012). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

The recombinant expression vectors may also contain a selectable marker gene which facilitates the selection of transformed or transfected host cells. Suitable selectable marker genes are genes encoding proteins such as G418 and hygromycin that confer resistance to certain drugs, β-galactosidase, chloramphenicol acetyltransferase, firefly luciferase, or an immunoglobulin or portion thereof such as the Fc portion of an immunoglobulin preferably IgG. The selectable markers may be introduced on a separate vector from the nucleic acid of interest.

Following the generation of the antisense nucleic acid, a skilled artisan will understand that the antisense nucleic acid will have certain characteristics that can be modified to improve the antisense nucleic acid as a therapeutic compound. Therefore, the antisense nucleic acid may be further designed to resist degradation by modifying it to include phosphorothioate, or other linkages, methylphosphonate, sulfone, sulfate, ketyl, phosphorodithioate, phosphoramidate, phosphate esters, and the like (see, e.g., Agrwal et al., 1987, Tetrahedron Lett. 28:3539-3542; Stec et al., 1985 Tetrahedron Lett. 26:2191-2194; Moody et al., 1989 Nucleic Acids Res. 12:4769-4782; Eckstein, 1989 Trends Biol. Sci. 14:97-100; Stein, In: Oligodeoxynucleotides. Antisense Inhibitors of Gene Expression, Cohen, ed., Macmillan Press, London, pp. 97-117 (1989)).

Any polynucleotide may be further modified to increase its stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queosine, and wybutosine and the like, as well as acetyl-methyl-, thio- and other modified forms of adenine, cytidine, guanine, thymine, and uridine.

In certain embodiments of the invention, an antisense nucleic acid sequence that is expressed by a plasmid vector is used to inhibit ATM or Chk2 protein expression. The antisense expressing vector is used to transfect a mammalian cell or the mammal itself, thereby causing reduced endogenous expression of ATM or Chk2.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue, 1993, U.S. Pat. No. 5,190,931.

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see U.S. Pat. No. 5,023,243).

In certain embodiments of the invention, a ribozyme is used to inhibit ATM or Chk2 protein expression. Ribozymes useful for inhibiting the expression of a target molecule may be designed by incorporating target sequences into the basic ribozyme structure which are complementary, for example, to the mRNA sequence encoding ATM or Chk2 Ribozymes targeting ATM or Chk2, may be synthesized using commercially available reagents (Applied Biosystems, Inc., Foster City, Calif.) or they may be genetically expressed from DNA encoding them.

In certain embodiments, the gene(s) producing the targeted protein(s) can be partially or completely excised from a cell, tissue and/or organ using a gene-editing technology. Several gene editing technologies are known in the art and can be used to change or alter gene expression. Non limiting examples include zinc finger nucleases (ZFN), transcription activator-like effector nucleases (TALENs), piggyback, and clustered regularly interspaced short palindromic repeats (CRISPR)/CRISPR-associated (Cas) system. In certain embodiments, the invention utilizes the CRISPR/Cas 9 system.

In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., 1987, J. Bacteriol. 169:5429-5433; Nakata et al., 1989, J. Bacteriol. 171:3553-3556), and associated genes. Similar interspersed SSRs have been identified in other bacteria (Groenen et al., 1993, Mol. Microbiol. 10:1057-1065; Hoe et al., 1999, Emerg. Infect. Dis. 5:254-263; Masepohl et al., 1996, Biochim. Biophys. Acta 1307:

26-30; Mojica et al., 1995, Mol. Microbiol. 17:85-93). The CRISPR loci typically differ from other SSRs by the structure of the repeats, which have been termed short regularly spaced repeats (SRSRs) (Janssen et al., 2002, OMICS J. Integ. Biol. 6:23-33; Mojica et al., 2000, Mol. Microbiol. 36:244-246). In general, the repeats are short elements that occur in clusters that are regularly spaced by unique intervening sequences with a substantially constant length. Although the repeat sequences are highly conserved between strains, the number of interspersed repeats and the sequences of the spacer regions typically differ from strain to strain (van Embden et al., 2000, J. Bacteriol. 182:2393-2401). CRISPR loci have been identified in more than 40 prokaryotes (Jansen et al., 2002, Mol. Microbiol. 43:1565-1575).

In general, "CRISPR system" refers collectively to transcripts and other elements involved expressing, or directing the activity of, CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. In general, a CRISPR system is characterized by elements that promote the formation of a CRISPR complex at the site of a target sequence (also referred to as a protospacer in the context of an endogenous CRISPR system).

In the context of formation of a CRISPR complex, "target sequence" refers to a sequence to which a guide sequence is designed to have some complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides. In certain embodiments, a target sequence is located in the nucleus or cytoplasm of a cell. In other embodiments, the target sequence may be within an organelle of a eukaryotic cell, for example, mitochondrion or nucleus. Typically, in the context of an endogenous CRISPR system, formation of a CRISPR complex (comprising a guide sequence hybridized to a target sequence and complexed with one or more Cas proteins) results in cleavage of one or both strands in or near (e.g., within about 1, 2, 3, 4, 5, 6, 7, 8, 9, 10, 20, 50 or more base pairs) the target sequence. As with the target sequence, it is believed that complete complementarity is not needed, provided this is sufficient to be functional. In certain embodiments, the tracr sequence has at least 50%, 60%, 70%, 80%, 90%, 95% or 99% of sequence complementarity along the length of the tracr mate sequence when optimally aligned. In other embodiments, one or more vectors driving expression of one or more elements of a CRISPR system are introduced into a host cell, such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In certain embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g., each in a different intron, two or more in at least one intron, or all in a single intron).

In general, a guide sequence is any polynucleotide sequence having sufficient complementarity with a target polynucleotide sequence to hybridize with the target sequence and direct sequence-specific binding of a CRISPR complex to the target sequence. In certain embodiments, the degree of complementarity between a guide sequence and its corresponding target sequence, when optimally aligned using a suitable alignment algorithm, is at least about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (maq dot sourceforge dot net). In certain embodiments, a guide sequence is at least about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In other embodiments, a guide sequence is less than about 75, 50, 45, 40, 35, 30, 25, 20, 15, 12, or fewer nucleotides in length. In yet other embodiments, a guide sequence is about 23 nucleotides in length.

The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex (including the guide sequence to be tested and a control guide sequence different from the test guide sequence), and comparing binding or rate of cleavage at the target sequence between the test and control guide sequence reactions. Other assays are contemplated by those skilled in the art. A guide sequence may be selected to target any target sequence. In certain embodiments, the target sequence is a sequence within a genome of a cell. Exemplary target sequences include those that are unique in the target genome. For example, for the S. pyogenes Cas9, a unique target sequence in a genome may include a Cas9 target site of the form MMMMMMMMNNNNNNNNNNNXGG where NNNNNNNNNNNXGG (N is A, G, T, or C; and X can be anything) has a single occurrence in the genome.

In certain embodiments, the guide sequence is a guide RNA (gRNA, or guiding RNA). The gRNA interacts with the CRISPR/Cas to guide it to a specific target site, wherein the effector domain of the CRISPR/Cas modifies the chromosomal sequence or regulates expression of the chromosomal sequence. Each guide RNA comprises three regions: a first region at the 5'-end that is complementary to the target site in the chromosomal sequence, a second internal region that forms a stem loop structure, and a third 3'-region that remains essentially single-stranded.

The first region of each guide RNA is distinct, such that each guide RNA guides a fusion protein to a specific target site. The second and third regions of each guide RNA can be the same in all guide RNAs. The first region of the guide RNA is complementary to the target site in the chromosomal sequence, such that the first region of the guide RNA can base pair with the target site. In certain embodiments, the first region of the guide RNA can comprise from about 10 nucleotides to more than about 25 nucleotides. For example, the region of base pairing between the first region of the guide RNA and the target site in the chromosomal sequence can be about 10, 11, 12, 13, 14, 15, 16, 17, 18, 19, 20, 22, 23, 24, 25, or more than 25 nucleotides in length. In other embodiments, the first region of the guide RNA is about 20 nucleotides in length. In yet other embodiments, the first region of the guide RNA is about 18 nucleotides in length. In yet other embodiments, the gRNAs are unique to the gene of interest.

The guide RNA also comprises a second region that forms a secondary structure. In certain embodiments, the secondary structure comprises a stem (or hairpin) and a loop. The length of the loop and the stem can vary. For example, the loop can range from about 3 to about 10 nucleotides in length, and the stem can range from about 6 to about 20 base pairs in length. The stem can comprise one or more bulges of 1 to about 10 nucleotides. Thus, the overall length of the second region can range from about 16 to about 60 nucleotides in length. In an exemplary embodiment, the loop is about 4 nucleotides in length and the stem comprises about 12 base pairs.

The guide RNA also comprises a third region at the 3' end that remains essentially single-stranded. Thus, the third region has no complementarity to any chromosomal sequence in the cell of interest and has no complementarity to the rest of the guide RNA. The length of the third region can vary. In general, the third region is more than about 4 nucleotides in length. For example, the length of the third region can range from about 5 to about 30 nucleotides in length.

In other embodiments, the guide RNA can comprise two separate molecules. The first RNA molecule can comprise the first region of the guide RNA and one half of the "stem" of the second region of the guide RNA. The second RNA molecule can comprise the other half of the "stem" of the second region of the guide RNA and the third region of the guide RNA. Thus, in this embodiment, the first and second RNA molecules each contain a sequence of nucleotides that are complementary to one another. For example, in certain embodiments, the first and second RNA molecules each comprise a sequence (of about 6 to about 20 nucleotides) that base pairs to the other sequence. In the embodiments where the guide RNA is introduced into the cell as a DNA molecule, the guide RNA coding sequence can be operably linked to promoter control sequence for expression of the guide RNA in the eukaryotic cell. For example, the RNA coding sequence can be operably linked to a promoter sequence that is recognized by RNA polymerase III (Pol III). Examples of suitable Pol III promoters include, but are not limited to, mammalian U6 or H1 promoters. In exemplary embodiments, the RNA coding sequence is linked to a mouse or human U6 promoter. In other exemplary embodiments, the RNA coding sequence is linked to a mouse or human H1 promoter. The DNA molecule encoding the guide RNA can be linear or circular.

In certain embodiments, the DNA sequence encoding the guide RNA can be part of a vector. Suitable vectors include plasmid vectors, phagemids, cosmids, artificial/mini-chromosomes, transposons, and viral vectors. In an exemplary embodiment, the DNA encoding the RNA-guided endonuclease is present in a plasmid vector. Non-limiting examples of suitable plasmid vectors include pUC, pBR322, pET, pBluescript, and variants thereof. The vector can comprise additional expression control sequences (e.g., enhancer sequences, Kozak sequences, polyadenylation sequences, transcriptional termination sequences, and so forth), selectable marker sequences (e.g., antibiotic resistance genes), origins of replication, and the like.

In certain embodiments, the number of gRNAs useful within the present invention ranges from about 1 to 25. In other embodiments, the number of gRNAs ranges from about 1 to 10. In yet other embodiments, the number of gRNAs ranges from about 1 to 8.

In certain embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Additional domains that may form part of a fusion protein comprising a CRISPR enzyme are described in US2011/0059502, incorporated herein by reference. In certain embodiments, a tagged CRISPR enzyme is used to identify the location of a target sequence.

In certain embodiments, a CRISPR enzyme in combination with (and optionally complexed with) a guide sequence is delivered to a cell. Conventional viral and non-viral based gene transfer methods can be used to introduce nucleic acids in mammalian cells or target tissues. Such methods can be used to administer nucleic acids encoding components of a CRISPR system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell (Anderson, 1992, Science 256:808-813; and Yu et al., 1994, Gene Therapy 1:13-26).

The complex CRISPR/Cas proteins can be derived from a CRISPR/Cas type I, type II, or type III system. Non-limiting examples of suitable CRISPR/Cas proteins include Cas3, Cas4, Cas5, Cas5e (or CasD), Cas6, Cas6e, Cas6f, Cas7, Cas8a1, Cas8a2, Cas8b, Cas8c, Cas9, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu1966. In certain embodiments, one or more elements of a CRISPR system is derived from a type I, type II, or type III CRISPR system.

In certain embodiments, the CRISPR/Cas is derived from a type II CRISPR/Cas system. In other embodiments, the CRISPR/Cas system is derived from a Cas9 protein. The Cas9 protein can be from *Streptococcus pyogenes, Streptococcus thermophilus, Streptococcus* sp., *Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum the rmopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus,* or *Acaryochloris marina.*

In general, CRISPR/Cas proteins comprise at least one RNA recognition and/or RNA binding domain. RNA recognition and/or RNA binding domains interact with the guiding RNA. CRISPR/Cas proteins can also comprise nuclease domains (i.e., DNase or RNase domains), DNA binding domains, helicase domains, RNAse domains, protein-protein interaction domains, dimerization domains, as well as other domains. The CRISPR/Cas proteins can be modified to increase nucleic acid binding affinity and/or specificity, alter an enzymatic activity, and/or change another property of the protein. In certain embodiments, the CRISPR/Cas-like protein of the fusion protein can be derived from a wild type Cas9 protein or fragment thereof. In other embodiments, the CRISPR/Cas can be derived from modified Cas9 protein. For example, the amino acid sequence of the Cas9 protein can be modified to alter one or more properties (e.g., nuclease activity, affinity, stability, and so forth) of the protein. Alternatively, domains of the Cas9 protein not involved in RNA-guided cleavage can be eliminated from the protein such that the modified Cas9 protein is smaller than the wild type Cas9 protein. In general, a Cas9 protein comprises at least two nuclease (i.e., DNase) domains. For example, a Cas9 protein can comprise a RuvC-like nuclease domain and a FINE-like nuclease domain. The RuvC and HNH domains work together to cut single strands to make a double-stranded break in DNA (Jinek et al., 2012, Science, 337:816-821). In certain embodiments, the Cas9-derived protein can be modified to contain only one functional nuclease domain (either a RuvC-like or a FINE-like nuclease domain). For example, the Cas9-derived protein can be modified such that one of the nuclease domains is deleted or mutated such that it is no longer functional (i.e., the nuclease activity is absent). In some embodiments in which one of the nuclease domains is inactive, the Cas9-derived protein is able to introduce a nick into a double-stranded nucleic acid (such protein is termed a "nickase"), but not cleave the double-stranded DNA. In any of the above-described embodiments, any or all of the nuclease domains can be inactivated by one or more deletion mutations, insertion mutations, and/or substitution mutations using well-known methods, such as site-directed mutagenesis, PCR-mediated mutagenesis, and total gene synthesis, as well as other methods known in the art.

The present invention also includes a vector driving the expression of the CRISPR system. The art is replete with suitable vectors that are useful in the present invention. The vectors to be used are suitable for replication and, optionally, integration in eukaryotic cells. Typical vectors contain transcription and translation terminators, initiation sequences, and promoters useful for regulation of the expression of the desired nucleic acid sequence. The vectors of the present invention may also be used for nucleic acid standard gene delivery protocols. Methods for gene delivery are known in the art (U.S. Pat. Nos. 5,399,346, 5,580,859 & 5,589,466, incorporated by reference herein in their entireties).

Further, the vector may be provided to a cell in the form of a viral vector. Viral vector technology is well known in the art and is described, for example, in Sambrook et al. (4$^{th}$ Edition, Molecular Cloning: A Laboratory Manual, Cold Spring Harbor Laboratory, New York, 2012), and in other virology and molecular biology manuals. Viruses, which are useful as vectors include, but are not limited to, retroviruses, adenoviruses, adeno-associated viruses, herpes viruses, Sindbis virus, gammaretrovirus and lentiviruses. In general, a suitable vector contains an origin of replication functional in at least one organism, a promoter sequence, convenient restriction endonuclease sites, and one or more selectable markers (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In certain embodiments, adenovirus vectors are used. In certain embodiments, lentivirus vectors are used.

In certain embodiments, the herpes-infected human is treated by antiviral therapy. In certain embodiments, the gene excision with the CRISPR/Cas9 system is performed on a human that has received, is receiving or will receive anti-herpes treatment. In certain embodiments, the anti-herpes treatment is continued, modified or terminated after gene excision with the CRISPR/Cas9 system.

In certain embodiments, a composition of isolated set of guide RNAs (gRNAs) is provided. In other embodiments, the gRNAs set of this invention comprises gRNAs that are at least partially identical to a fragment of the gene that should be excised from the genomic DNA. In certain embodiments, the level of identity between the gRNA and its targeted region is determined by the degree of complementarity. In other embodiments, the degree of complementarity between a gRNA and its corresponding target sequence, when optimally aligned using a suitable alignment algorithm, is about or more than about 50%, 60%, 75%, 80%, 85%, 90%, 95%, 97.5%, 99%, or more.

Polypeptide Inhibitors

In certain embodiments, the invention includes an isolated peptide inhibitor that inhibits ATM or Chk2 In other embodiments, the peptide inhibitor of the invention inhibits ATM or Chk2 directly by binding to ATM or Chk2, thereby preventing the normal functional activity of ATM or Chk2 In yet other embodiments, the peptide inhibitor of the invention inhibits ATM or Chk2 by competing with endogenous ATM or Chk2 In yet other embodiments, the peptide inhibitor of the invention inhibits the activity of ATM or Chk2 by acting as a transdominant negative mutant.

The variants of the polypeptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the invention, (iv) fragments of the polypeptides, and/or (v) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

Antibody Inhibitors

The invention also contemplates an inhibitor of ATM or Chk2 comprising an antibody, or antibody fragment, specific for ATM or Chk2 That is, the antibody can inhibit ATM or Chk2 to provide a beneficial effect.

The antibodies may be intact monoclonal or polyclonal antibodies, and immunologically active fragments (e.g., a Fab or (Fab)$_2$ fragment), an antibody heavy chain, an antibody light chain, humanized antibodies, a genetically engineered single chain $F_V$ molecule (Ladner et al, U.S. Pat. No. 4,946,778), or a chimeric antibody, for example, an antibody that contains the binding specificity of a murine antibody, but in which the remaining portions are of human origin. Antibodies including monoclonal and polyclonal antibodies, fragments and chimeras, may be prepared using methods known to those skilled in the art.

Antibodies can be prepared using intact polypeptides or fragments containing an immunizing antigen of interest. The polypeptide or oligopeptide used to immunize an animal may be obtained from the translation of RNA or synthesized chemically and can be conjugated to a carrier protein, if desired. Suitable carriers that may be chemically coupled to peptides include bovine serum albumin and thyroglobulin, keyhole limpet hemocyanin. The coupled polypeptide may then be used to immunize the animal (e.g., a mouse, a rat, or a rabbit).

Methods

In one aspect, the present invention provides a method of treating or preventing herpes simplex labialis in a subject in need thereof. In another aspect, the present invention provides a method of treating or preventing herpes esophagitis in a subject in need thereof.

In certain embodiments, the method comprises administering to the subject an effective amount of an ATM inhibitor. In other embodiments, the method comprises administering to the subject an effective amount of a Chk2 inhibitor. In yet other embodiments, the method comprises administering to the subject an effective amount of a composition comprising an ATM inhibitor and an anti-herpetic agent. In yet other embodiments, the method comprises administering to the subject an effective amount of a composition comprising a Chk2 inhibitor and an anti-herpetic agent. In yet other embodiments, the method comprises administering to the subject an effective amount of a composition comprising an ATM inhibitor, a Chk2 inhibitor and optionally an anti-herpetic agent. In yet other embodiments, the method comprises administering to the subject an effective amount of an ATM inhibitor and an effective amount of an anti-herpetic agent. In yet other embodiments, the method comprises administering to the subject an effective amount of a Chk2 inhibitor and an effective amount of an anti-herpetic agent. In yet other embodiments, the method comprises administering to the subject an effective amount of a Chk2 inhibitor, an effective amount of an ATM inhibitor and optionally an effective amount of an anti-herpetic agent. In yet other embodiments, the compositions of the invention comprise a pharmaceutically acceptable carrier.

In certain embodiments, administration of an ATM inhibitor reduces the effective amount of the anti-herpetic agent required to be administered to the subject to obtain the same therapeutic benefit. In other embodiments, administration of a Chk2 inhibitor reduces the effective amount of the anti-herpetic agent required to be administered to the subject to obtain the same therapeutic benefit. In yet other embodiments, the reduced effective amount of the anti-herpetic agent required to be administered to the subject to obtain the same therapeutic benefit results in a reduced frequency or severity of side effects due to the anti-herpetic agent experienced by the subject. In yet other embodiments, the infection is caused by a drug-resistant HSV-1 strain. In yet other embodiments, the drug-resistant HSV-1 strain has a TK mutation. In yet other embodiments, the strain is resistant to at least one selected from the group consisting of acyclovir, famciclovir, penciclovir, valacyclovir, acyclovir, trifluridine, penciclovir and valacyclovir.

In certain embodiments, the ATM inhibitor is at least one selected from the group consisting of a nucleic acid, an antisense nucleic acid, an siRNA, a ribozyme, an shRNA, a peptide, an antibody, a small molecule, an antagonist, an aptamer, or a peptidomimetic that reduces the expression or activity of ATM. In other embodiments, the ATM inhibitor is selected from the group consisting of caffeine, wortmannin, chloroquine, CP-466722, KU-55933, KU-59403 and KU-60019, a salt or solvate thereof, and any combinations thereof.

In certain embodiments, the Chk2 inhibitor is at least one selected from the group consisting of a nucleic acid, an antisense nucleic acid, an siRNA, a ribozyme, an shRNA, a peptide, an antibody, a small molecule, an antagonist, an aptamer, or a peptidomimetic that reduces the expression or activity of Chk2 In other embodiments, the Chk2 inhibitor is Chk2 inhibitor II, SC-203885 or NSC-109555.

In certain embodiments, the anti-herpetic agent is at least one selected from the group consisting of acyclovir, famciclovir, penciclovir, valacyclovir, acyclovir, trifluridine, penciclovir and valacyclovir.

In certain embodiments, the composition comprises a combination of inhibitors described herein. For example, in certain embodiments the composition comprises a combination of an ATM inhibitor and a Chk2 inhibitor, in combination with an optional anti-herpetic agent.

ATM or Chk2 activity can be inhibited using any method known to the skilled artisan. Examples of methods that inhibit ATM or Chk2 activity, include but are not limited to, inhibiting expression of an endogenous gene encoding ATM or Chk2, decreasing expression of mRNA encoding ATM or Chk2, and inhibiting the function, activity, or stability of ATM or Chk2. An ATM or Chk2 inhibitor may therefore be a compound that decreases expression of a gene encoding ATM or Chk2, decreases RNA half-life, stability, or expression of a mRNA encoding ATM or Chk2 protein, or inhibits ATM or Chk2 function, activity or stability. An ATM or Chk2 inhibitor may be any type of compound, including but not limited to, a peptide, a nucleic acid, an antisense nucleic acid, an aptamer, a peptidometic, and a small molecule, or combinations thereof.

ATM or Chk2 inhibition may be accomplished either directly or indirectly. For example ATM or Chk2 may be directly inhibited by compounds or compositions that directly interact with ATM or Chk2, such as antibodies. Alternatively, ATM or Chk2 may be inhibited indirectly by compounds or compositions that inhibit ATM or Chk2 downstream effectors, or upstream regulators which up-regulate ATM or Chk2 expression.

Decreasing expression of an endogenous gene includes providing a specific inhibitor of gene expression. Decreasing expression of mRNA or protein includes decreasing the half-life or stability of mRNA or decreasing expression of mRNA. Methods of decreasing expression of ATM or Chk2 include, but are not limited to, methods that use an siRNA, a microRNA, an antisense nucleic acid, a ribozyme, an expression vector encoding a transdominant negative mutant, a peptide, a small molecule, and combinations thereof.

Administration

The invention also encompasses the use of pharmaceutical compositions of at least one composition of the invention or a salt thereof to practice the methods of the invention. Such a pharmaceutical composition may consist of at least one composition of the invention or a salt thereof, in a form suitable for administration to a subject, or the pharmaceutical composition may comprise at least one composition of the invention or a salt thereof, and one or more pharmaceutically acceptable carriers, one or more additional ingredients, or some combination of these. The at least one composition of the invention may be present in the pharmaceutical composition in the form of a physiologically acceptable salt, such as in combination with a physiologically acceptable cation or anion, as is well known in the art.

Administration of an ATM inhibitor, a Chk2 inhibitor, or an anti-herpetic agent in a method of treatment can be achieved in a number of different ways, using methods known in the art. The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered.

In certain embodiments, the composition is administered to the subject by an intrapulmonary, intrabronchial, inhalational, intranasal, intratracheal, intravenous, intramuscular, subcutaneous, topical, transdermal, oral, buccal, rectal, pleural, peritoneal, vaginal, epidural, otic, intraocular, or intrathecal route. In other embodiments, the composition is administered to the subject by a topical, transdermal, oral or buccal route.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

In various embodiments, an ATM inhibitor and an anti-herpetic agent, or a Chk2 inhibitor and an anti-herpetic agent, are administered to a subject. The inhibitor may also be a hybrid or fusion composition to facilitate, for instance, delivery to target cells or efficacy. In certain embodiments, a hybrid composition may comprise a tissue-specific targeting sequence.

The therapeutic and prophylactic methods of the invention thus encompass the use of pharmaceutical compositions of the invention to practice the methods of the invention. The pharmaceutical compositions useful for practicing the invention may be administered to deliver a dose to the subject of from 1 ng/kg/day and 100 mg/kg/day. In certain embodiments, the invention envisions administration of a dose which results in a concentration of the compound of the invention from 1 µM and 10 µM in a mammal.

Typically, dosages which may be administered in a method of the invention to a mammal, preferably a human, range in amount from 0.5 µg to about 50 mg per kilogram of body weight of the mammal, while the precise dosage administered will vary depending upon any number of factors, including but not limited to, the type of mammal and type of disease state being treated, the age of the mammal and the route of administration. Preferably, the dosage of the compound will vary from about 1 µg to about 10 mg per kilogram of body weight of the mammal. More preferably, the dosage will vary from about 3 µg to about 1 mg per kilogram of body weight of the mammal.

Compositions of the invention for administration may be in the range of from about 1 µg to about 1,000 mg, about 2 µg to about 500 mg, about 4 µg to about 250 mg, about 6 µg to about 200 mg, about 8 µg to about 100 mg, about 10 µg to about 50 mg, about 20 µg to about 25 mg, about 40 µg to about 10 mg, about 50 µg to about 5 mg, about 100 µg to about 1 mg, and any and all whole or partial increments thereinbetween.

In some embodiments, the dose of a composition of the invention is from about 0.5 µg and about 2,000 mg. In some embodiments, a dose of a composition described herein is less than about 2,000 mg, or less than about 1,000 mg, or less than about 500 mg, or less than about 250 mg, or less than about 100 mg, or less than about 50 mg, or less than about 25 mg, or less than about 10 mg, or less than about 5 mg, or less than about 1 mg, and any and all whole or partial increments thereof.

The compound may be administered to a mammal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the mammal, etc.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition.

Suitable compositions and dosage forms include, for example, suspensions, granules, beads, powders, pellets, and liquid sprays for nasal administration, dry powder or aerosolized formulations for inhalation, and the like. It should be understood that the formulations and compositions that would be useful in the present invention are not limited to the particular formulations and compositions that are described herein. For example, formulations may comprise a powder or an aerosolized or atomized solution or suspension comprising the active ingredient. Such powdered, aerosolized, or aerosolized formulations may further comprise one or more of the additional ingredients described herein. The examples of formulations described herein are not exhaustive and it is understood that the invention includes additional modifications of these and other formulations not described herein, but which are known to those of skill in the art.

In certain embodiments, the invention includes a method comprising administering a combination of a kinase inhibitor and an anti-herpetic agent elsewhere described herein. In certain embodiments, the method has an additive effect, wherein the overall effect of the administering a combination of a kinase inhibitor and an anti-herpetic agent is approximately equal to the sum of the effects of administering each of the inhibitor or anti-herpetic agent alone. In other embodiments, the method has a synergistic effect, wherein the overall effect of administering a combination of a kinase inhibitor and an anti-herpetic agent is greater than the sum of the effects of administering each of the inhibitor or anti-herpetic agent alone.

The method comprises administering a combination of a kinase inhibitor and an anti-herpetic agent in any suitable ratio. For example, in various embodiments, the method comprises administering the inhibitor and the anti-herpetic agent at a 500:1 ratio, a 100:1 ratio, a 50:1 ration, a 10:1 ratio, a 1:1 ratio, a 1:10 ratio, a 1:50 ratio, a 1:100 ratio, or a 1:500, or any ratio therebetween. However, the method is not limited to any particular ratio. Rather, any ratio that is shown to be effective is encompassed.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the invention. Moreover, all values that fall within these ranges, as well as the upper or lower limits of a range of values, are also contemplated by the present application.

The following examples further illustrate aspects of the invention. However, they are in no way a limitation of the teachings or disclosure of the invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

Cells and Viruses

All cells were cultured at 37° C. and 5% $CO_2$ and supplemented with 100 U/mL penicillin and 100 U/mL streptomycin. OKF6/TERT2 human oral mucosal keratinocyte cells were cultured in GIBCO Keratinocyte serum free medium (K-sfm) supplemented with bovine pituitary extract, epidermal growth factor, and calcium chloride (Life Technologies Carlsbad, Calif.). These cells are immortalized by expression of hTERT (Dickson, et al., 2000, Mol. Cell. Biol. 20(4):1436-1447). EPC2 human esophageal epithelial cells were cultured in K-sfm (Carlsbad, Calif.). KOS strain (Smith, Proc. Soc. Exp. Biol. Med. Soc. Exp. Biol. Med. 115:814-816) of HSV-1 was used in all infections. All viral stocks were titered on CV-1 monolayers.

Infection and Treatments of Cultured Cells

Subconfluent monolayers of cells were grown in six-well plates. Drug treatments were administered 60 minutes prior to infection and continued for the entire duration of each experiment. Infections with KOS strain of HSV-1 were carried out in six-well plates in a 200 µL inoculum volume at 37° C. for 1 hour with intermittent rocking. The cells were then rinsed and overlaid with fresh medium.

Unless indicated otherwise, KU-55933 (Batch No. 5, 99.7% purity; Tocris Bioscience, Bristol, UK) and Chk2 Inhibitor II (Sigma-Aldrich, St. Louis, Mo.) were used at 10 µM final concentration, phosphonoacetic acid (PAA) at 400 µg/mL (Sigma-Aldrich, St. Louis, Mo.), and acyclovir at 50 µg/mL (Sigma-Aldrich). KU-55933 and Chk2 Inhibitor II were dissolved in dimethyl sulfoxide (DMSO), and the final concentration of DMSO for KU-55933, Chk2 Inhibitor II, and mock treatments for all in vitro experiments was 0.1%.

Viral Genome Replication and Transcription

Viral genome replication and transcription were measured by quantitative PCR (qPCR). Total DNA and RNA from infected cells were isolated using the DNeasy Blood & Tissue Kit and the RNeasy Mini Kit, respectively (QIAGEN, Hilden, Germany). RNA was converted to cDNA using qScript (Quanta BioSciences, Gaithersburg, Md.). Real-time qPCR was performed with SYBR Green (Bio-Rad, Hercules, Calif.). Target primers for UL30 (DNA polymerase catalytic subunit) and reference primers for glyceraldehyde 3-phosphate dehydrogenase (GAPDH) were used to measure genome replication. Transcription of the three gene families was measured with primers for RL2 (ICP0), UL30 (DNA polymerase catalytic subunit), UL23 (thymidine kinase), and UL44 (gC), with reference primers for the 18S ribosomal RNA (rRNA).

Western Blot

Standard protocol was followed for Western blot analysis. Cell lysates were collected in 200 µL Laemmli buffer, vortexed, and boiled at 95° C. for 5 minutes. Protein concentrations were measured by bicinchoninic acid (BCA) assay. SDS-PAGE was followed by transfer onto a polyvinylidene difluoride (PVDF) membrane, which was then blocked in 5% BSA. Primary antibodies against the following proteins were used: ICP0 (mouse monoclonal; Virusys Corporation, Taneytown, Md.), ICP4 and nucleolin (both mouse monoclonal; Santa Cruz Biotechnology, Santa Cruz, Calif.), ICP8 (rabbit polyclonal), glycoprotein B and C (mouse monoclonal and rabbit polyclonal, respectively), ATM and pATM S1981 (rabbit polyclonal and mouse monoclonal, respectively; Rockland), Chk2 and pChk2 T68 (rabbit polyclonal and mouse monoclonal, respectively; Cell Signaling). Blots were stained with secondary antibodies and visualized with the Odyssey near-infrared system (LI-COR, Lincoln, Nebr.).

Statistical Analysis

Statistical significance was determined using Student's t-test and is indicated as ns (P>0.05), *(P<0.05), (P<0.01), or *(P<0.001).

Example

Figure 4A:
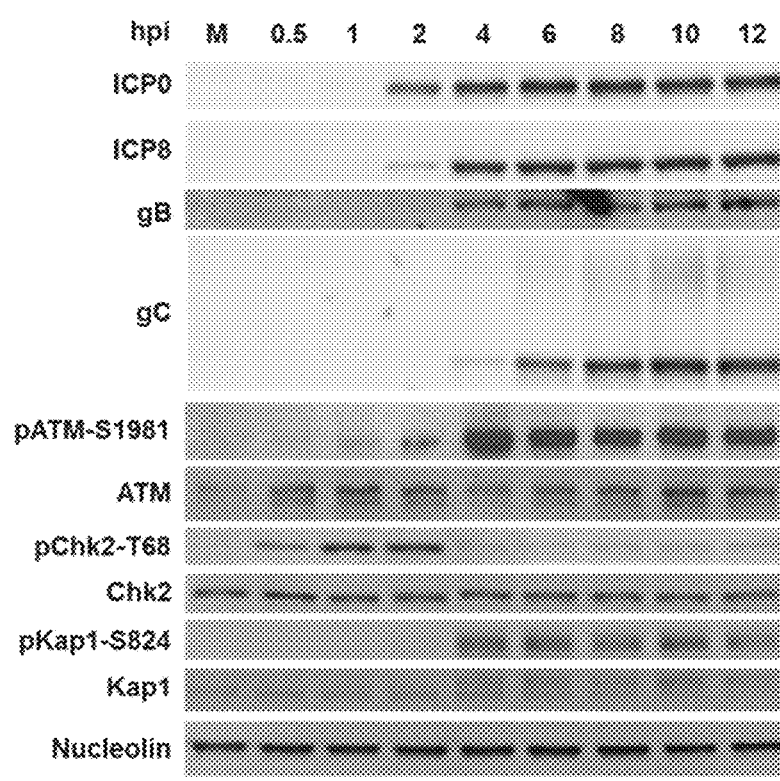
FIGS. 4A-4B comprise a series of images illustrating the activation of ATM following HSV-1 infection of OKF6 cells (MOI=5.0).
Figure 4B:
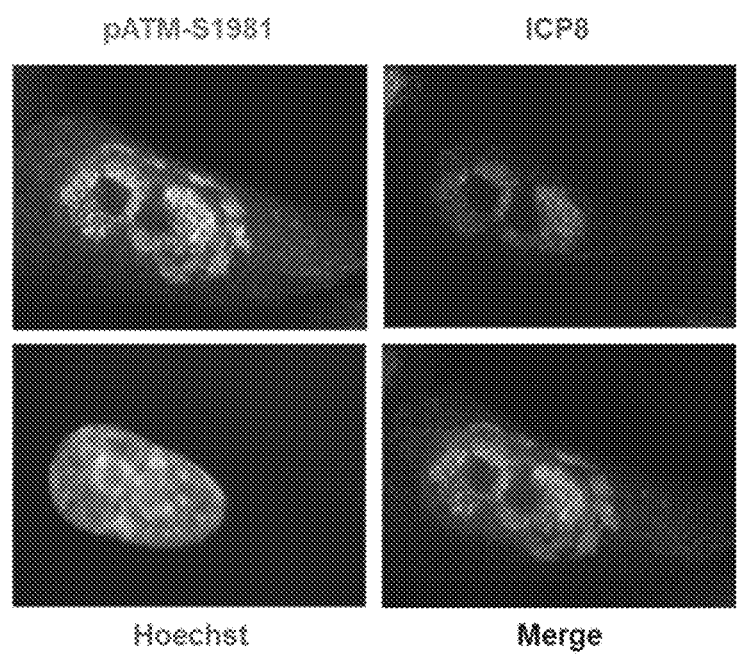
Figure 5:
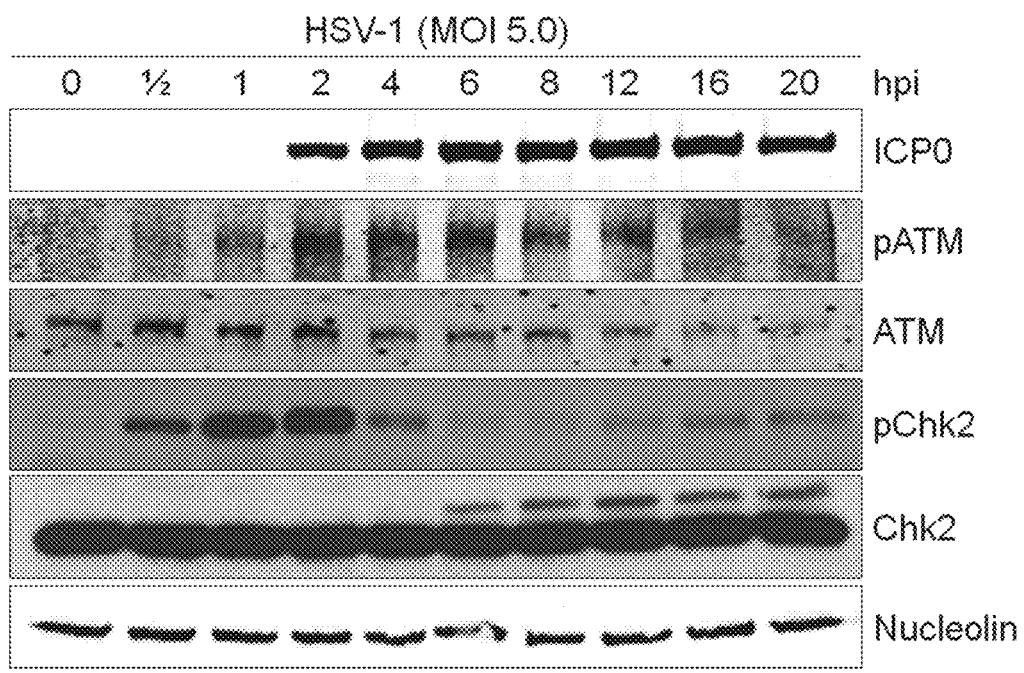
FIG. 5 comprises a series of images illustrating the activation of ATM following HSV-1 infection of EPC2 cells (MOI=5.0).

The infection of OKF6 cells (FIGS. 4A-4B) and EPC2 cells (FIG. 5) with the HSV-1 strain KOS was evaluated. Following HSV-1 infection, ATM was activated as determined by an increase of autophosphorylation of ATM on serine residue 1981, and phosphorylation of two well characterized ATM targets, Chk2 and Kap1.

Figure 6:
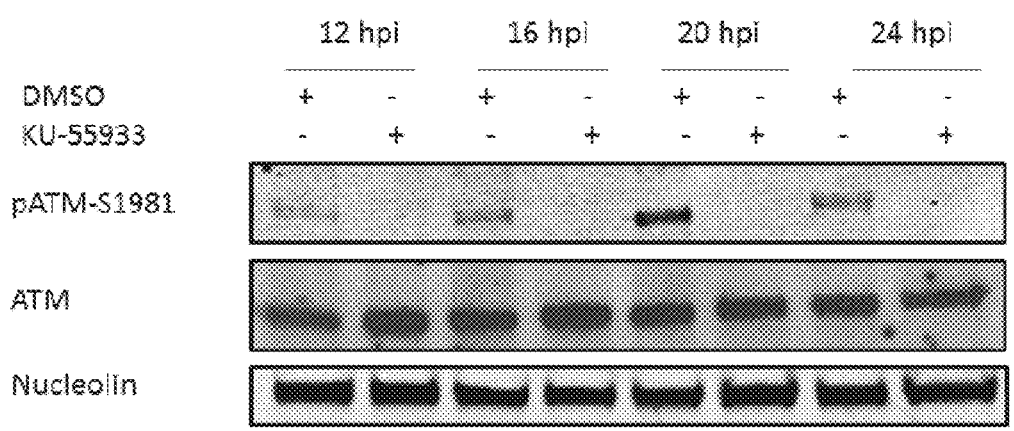
FIG. 6 comprises a series of images illustrating the finding that KU-55933 inhibits ATM activation in OKF6 cells (MOI=5.0).
Figure 7A:
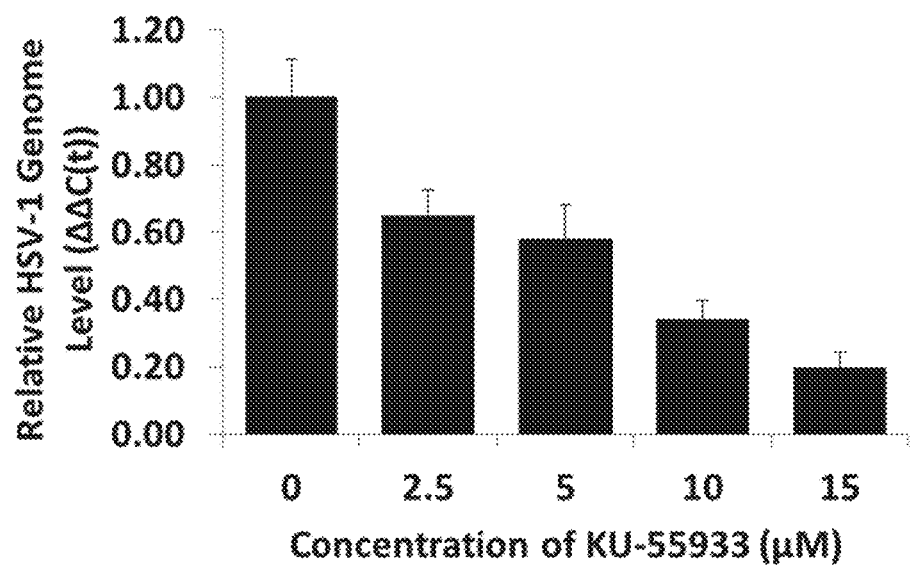
Figure 7B:
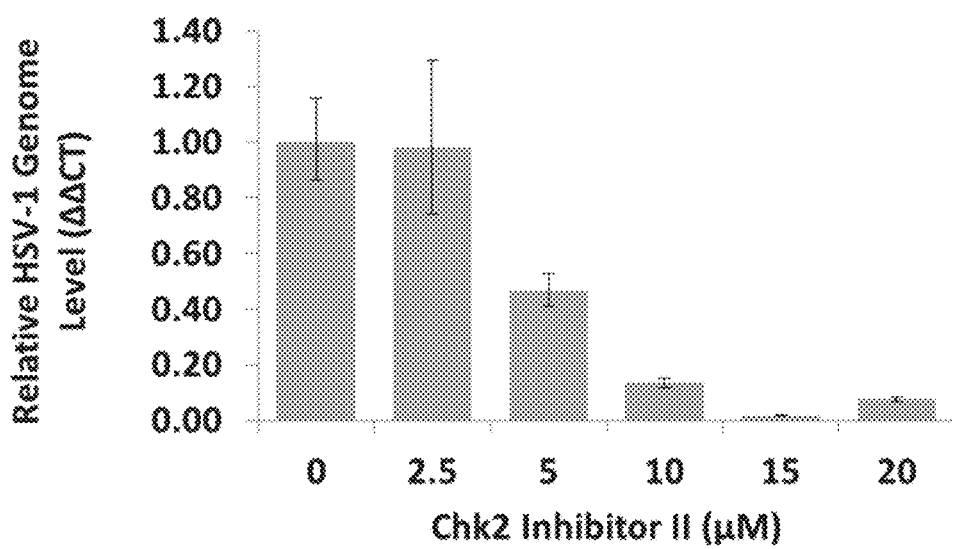
Figure 8A:
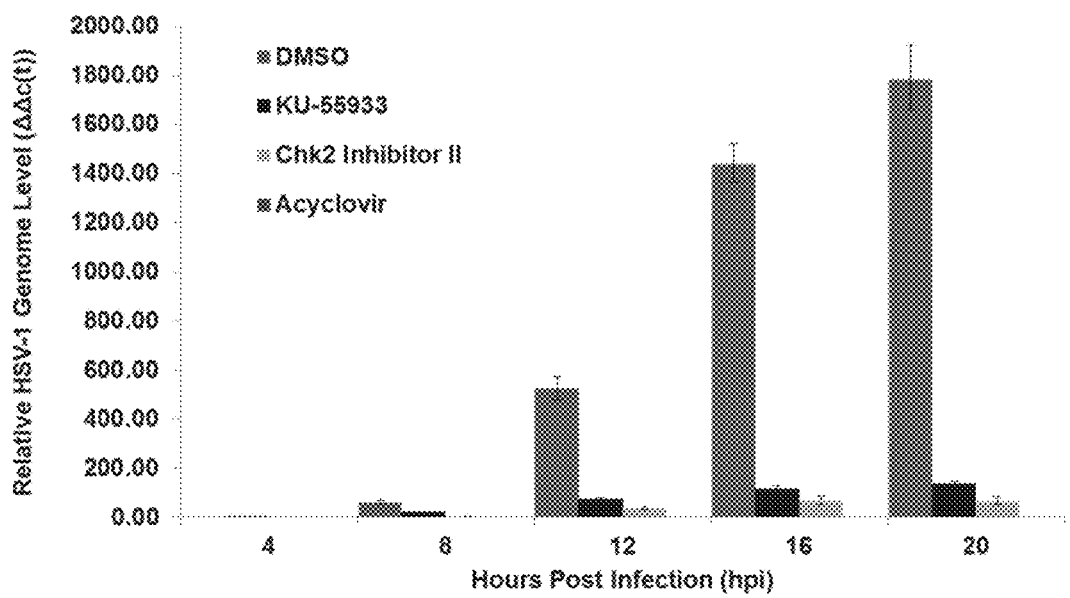
FIGS. 8A-8B comprise a set of graphs illustrating the fold change of HSV-1 genome copy number (FIG. 8A) and viral yield (FIG. 8B) as a function of hours post-infection (hpi) (MOI=0.1). KU-55933 and Chk2 Inhibitor II caused distinctive reductions in viral replication.
Figure 8B:
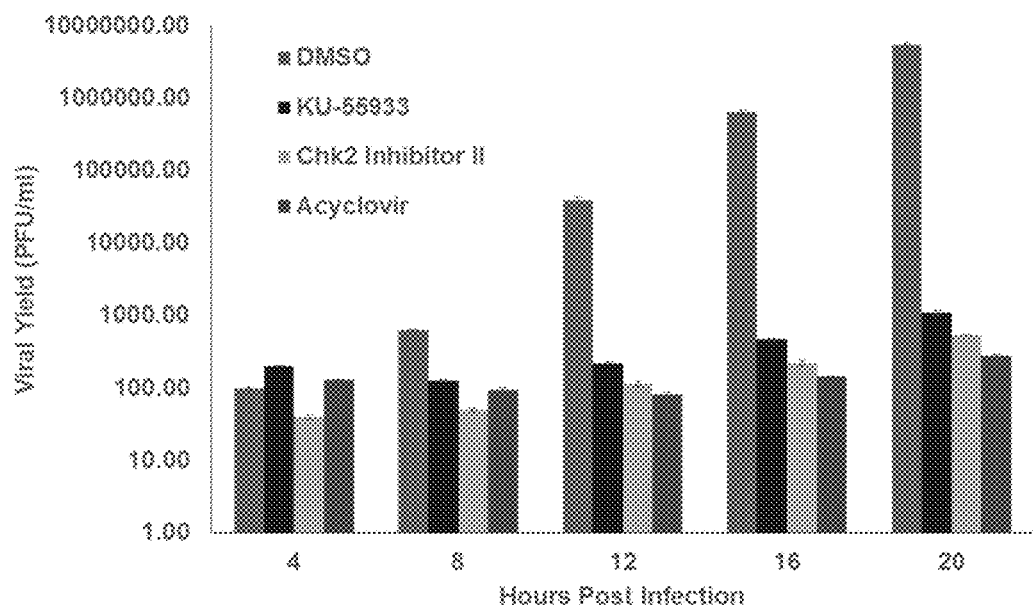

Treatment of HSV-1-infected cells with KU-55933 inhibited ATM activation in OKF6 cells (FIG. 6). Treatment of OKF6 with either KU-55933 or Chk2 Inhibitor II reduced HSV-1 replication in a dose dependent manner as measured by qPCR and viral yield. (FIGS. 7A-7C). Treatment of OKF6 with KU-55933 and Chk2 Inhibitor II also reduced HSV-1 replication throughout the entire time course of lytic infection (FIGS. 8A-8B).

Figure 9B:
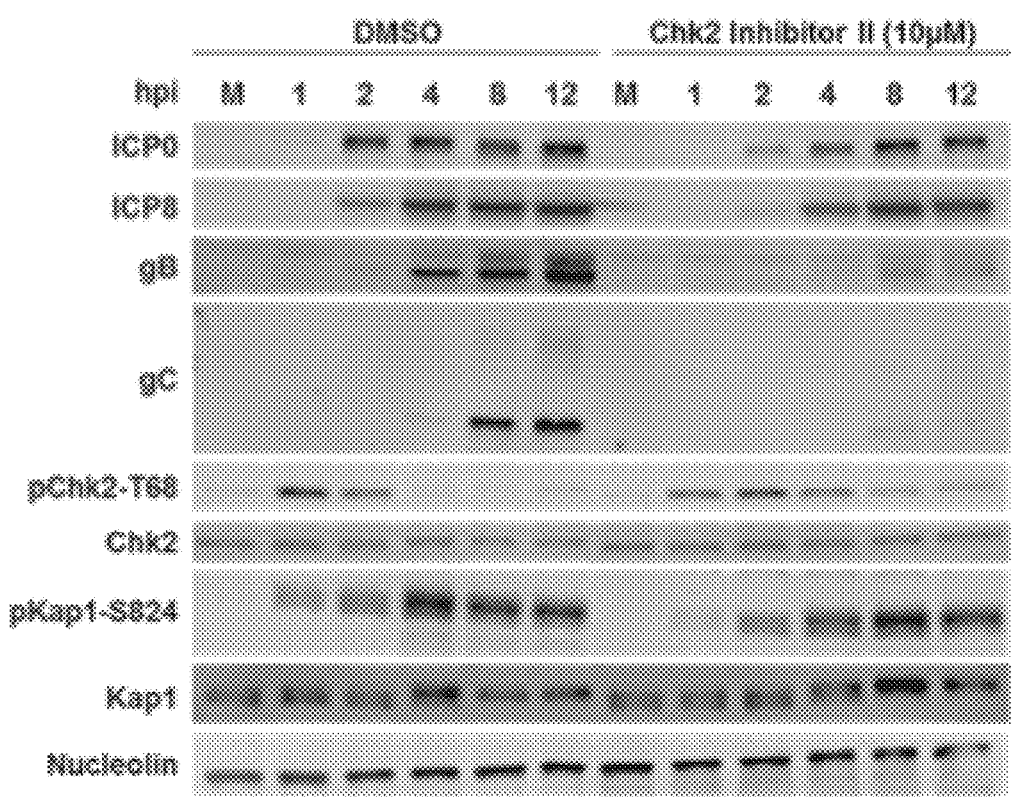
Figure 9C:
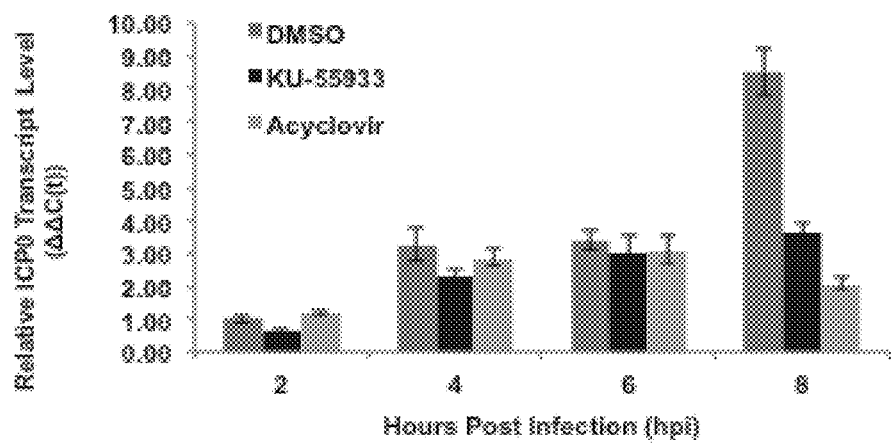
Figure 9D:
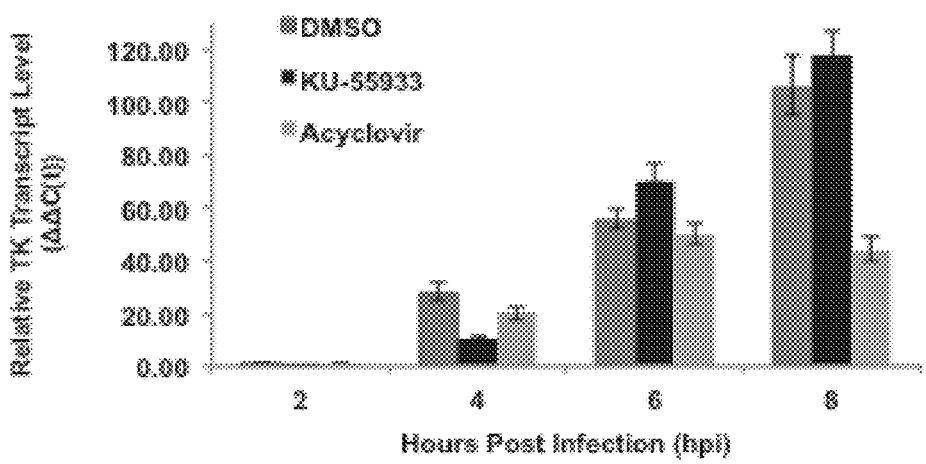
Figure 9E:
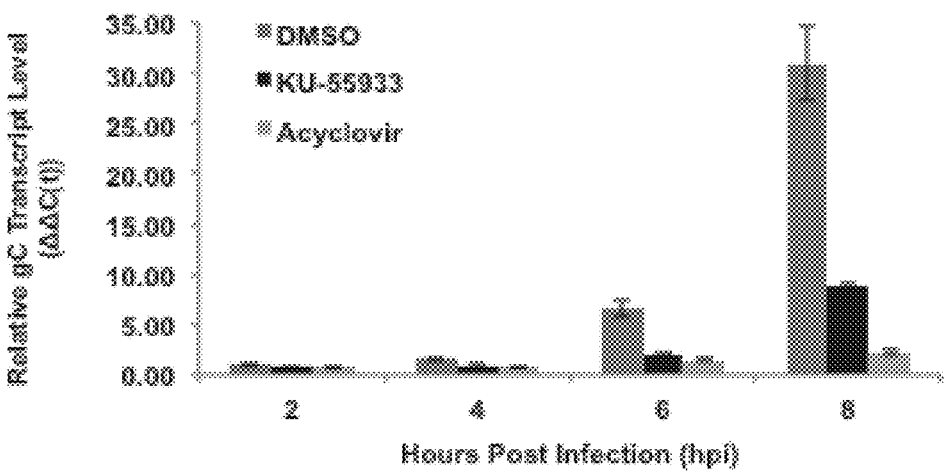

Inhibition of ATM or Chk2 in OKF6 cells through the administration of KU-55933 or Chk2 Inhibitor II, respectively, had no impact on the protein synthesis of HSV-1 immediate early (ICP0), early (ICP8), or leaky-late (gB) classes of genes, but resulted in a large reduction of the true-late gene gC (FIGS. 9A-9B). The reduction of the true-late gene gC by KU-55933 was determined to be at the level of gene transcription as measured by qPCR (FIG. 9E). The selective inhibition of the DNA replication-dependent true-late gene class suggests that KU-55933 and Chk2 Inhibitor II function by blocking HSV-1 DNA replication.

Figure 10A:
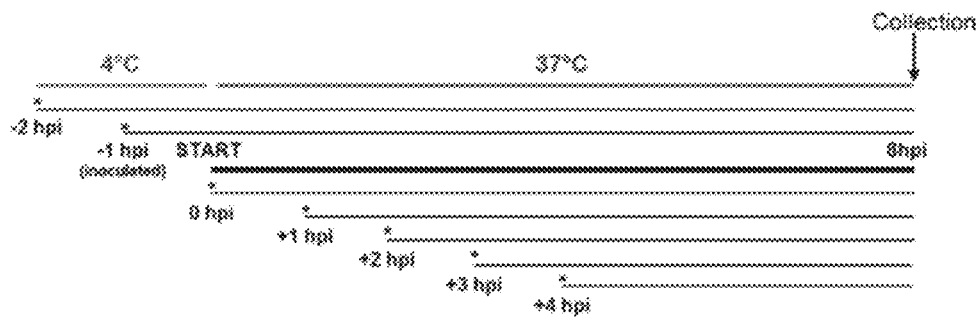
FIGS. 10A-10B comprise a set of images illustrating the effect of administration time for KU-55933 and Chk2 Inhibitor II on the expression of HSV-1 factors (MOI=5).
Figure 10B:
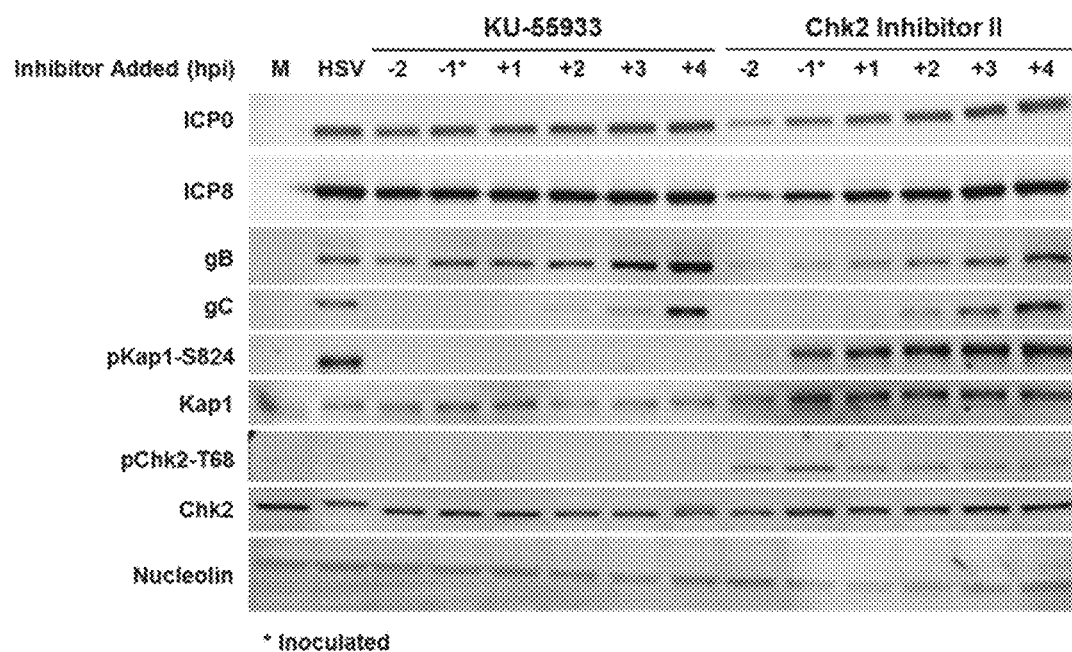

Treatment of OKF6 cells with KU-55933 or Chk2 Inhibitor II before infection or up to 1 hour post infection resulted in a large reduction of gC (FIGS. 10A-10B). Low levels of gC were produced when these inhibitors were applied between 2 to 3 hours post infection, and these inhibitors had no impact on gC levels (compared to wild type infection) when they were applied 4 hours post infection. This result illustrates that KU-55933 and Chk2 Inhibitor II impede a function within the first hour of infection that is necessary for full gC expression.

Figure 11A:
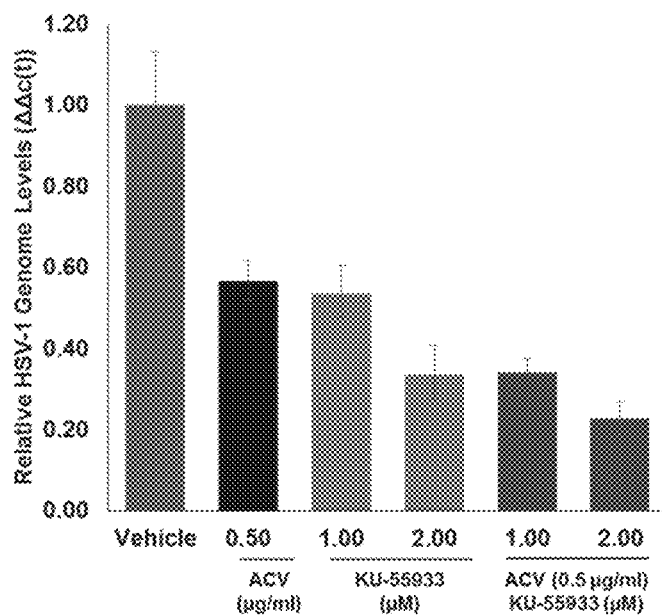
FIGS. 11A-11B comprise a set of graphs illustrating that KU-55933 and Chk2 Inhibitor II have a greater-than-additive effect on reducing HVS-1 replication when combined with acyclovir (MOI=0.1).
Figure 11B:
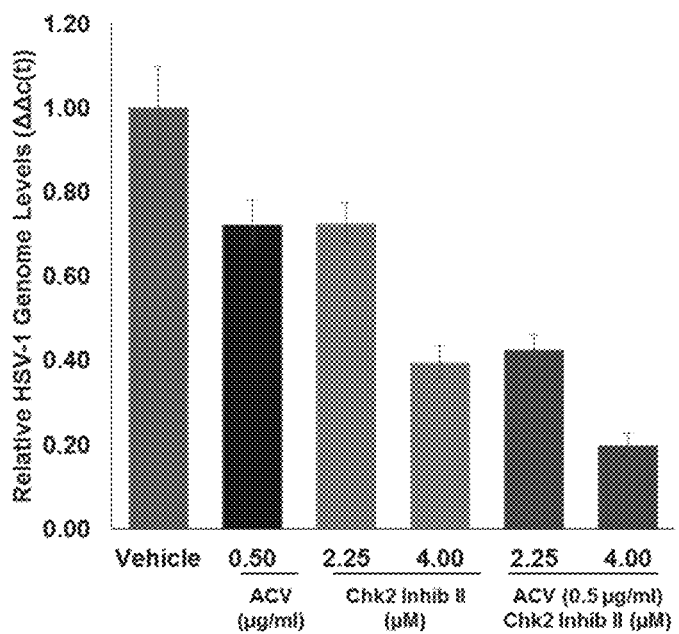
Figure 12A:
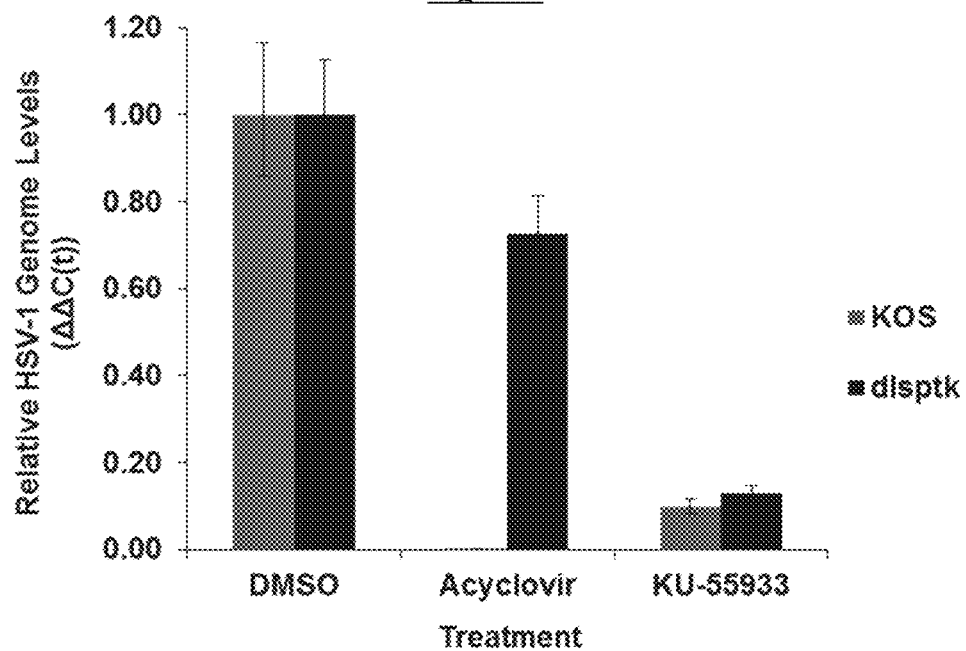
FIGS. 12A-12B comprise a set of graphs illustrating that KU-55933 and Chk2 Inhibitor II reduce HSV-1 genome copy numbers of an acyclovir-resistant strain of HSV-1 (MOI=0.1).
Figure 12B:
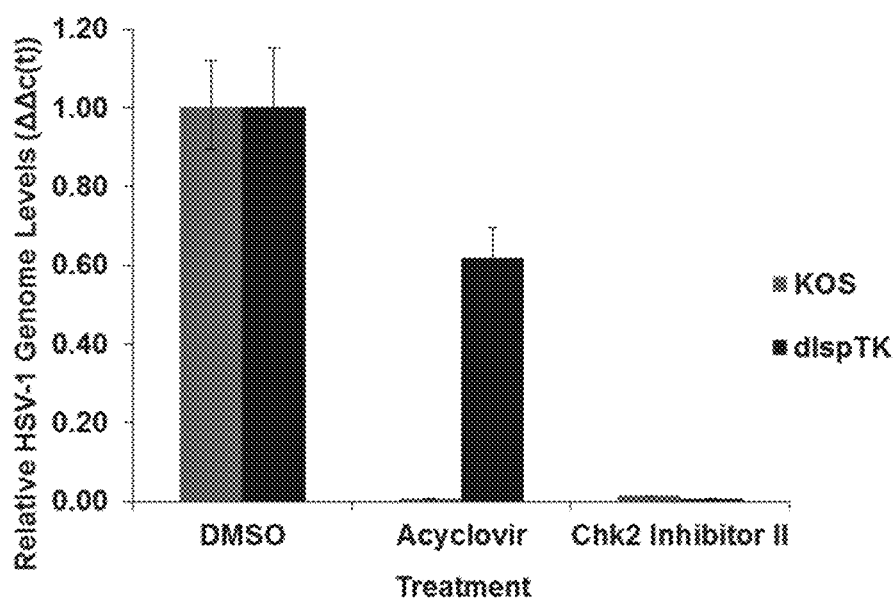

When low doses of KU-55933 and Chk2 Inhibitor II were combined with low doses of acyclovir, they had an additive to greater-than-additive effect on reducing HSV-1 replication in OKF6 cells (FIGS. 11A-11B). Treatment of OKF6 cells with KU-55933 and Chk2 Inhibitor II also greatly reduced replication of an acyclovir-resistant strain of HSV-1, dlspTK (FIGS. 12A-12B).

Figure 13A:
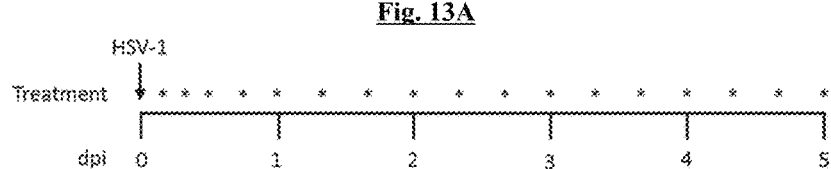
FIGS. 13A-13B comprise a set of images illustrating that KU-55933 and Chk2 Inhibitor II are effective at reducing the severity of clinical herpes simplex labialis symptoms when applied routinely to mice infected HSV-1.
Figure 13B:
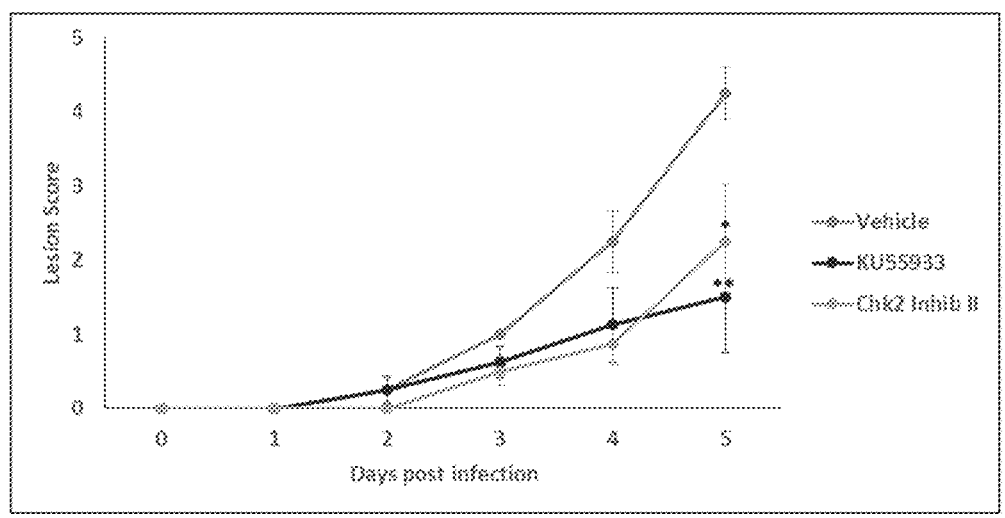

KU-55933 and Chk2 Inhibitor II were also efficacious at reducing HSV-1 in an in vivo model of infection (FIGS. 13A-13B). BALB/c mice were infected with HSV-1 on the lower lip, and KU-55933 or Chk2 Inhibitor II was applied every 4 hours for the first 12 hours post infection followed by treatments every 8 hours for the next 5 days. The mice were scored based on the severity of the symptoms, and tracked over the course of infection. Treatment with KU-55933 or Chk2 Inhibitor II produced a statistically significant decrease in the severity of symptoms during the time course of infection.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising acyclovir and KU-55933, or a salt, solvate or N-oxide thereof,
   wherein the acyclovir and the KU-55933 are present in the composition in a therapeutically effective amount that treats a HSV-1 infection in a subject in need thereof, and
   wherein the HSV-1 infection comprises at least one selected from the group consisting of herpes simplex labialis and herpes esophagitis.

2. A kit comprising a KU-55933, or a salt, N-oxide or solvate thereof, an applicator; acyclovir; and an instructional material for the use of the kit, wherein the instruction material comprises instructions for treating, ameliorating or preventing a HSV-1 infection in a subject in need thereof, wherein the HSV-1 infection comprises at least one selected from the group consisting of herpes simplex labialis and herpes esophagitis.

* * * * *